United States Patent
Okuma et al.

(10) Patent No.: US 10,260,057 B2
(45) Date of Patent: Apr. 16, 2019

(54) THERMOSTABLE CELLOBIOHYDROLASE

(71) Applicant: HONDA MOTOR CO., LTD., Minato-ku, Tokyo (JP)

(72) Inventors: Jiro Okuma, Wako (JP); Migiwa Suda, Kisarazu (JP); Asuka Yamaguchi, Tokyo (JP); Yoshitsugu Hirose, Wako (JP); Yasuhiro Kondo, Kawagoe (JP); Masaru Sato, Kisarazu (JP); Daisuke Shibata, Kisarazu (JP)

(73) Assignee: Honda Motor Co., Ltd., Tokyo (JP)

( * ) Notice: Subject to any disclaimer, the term of this patent is extended or adjusted under 35 U.S.C. 154(b) by 41 days.

(21) Appl. No.: 15/461,815

(22) Filed: Mar. 17, 2017

(65) Prior Publication Data

US 2017/0275605 A1 Sep. 28, 2017

(30) Foreign Application Priority Data

Mar. 28, 2016 (JP) ................................ 2016-064525

(51) Int. Cl.

| | | |
|---|---|---|
| *C12N 9/24* | (2006.01) | |
| *C12P 19/14* | (2006.01) | |
| *C12N 9/42* | (2006.01) | |
| *C12P 19/12* | (2006.01) | |
| *C12P 19/02* | (2006.01) | |

(52) U.S. Cl.
CPC ............ *C12N 9/2437* (2013.01); *C12P 19/02* (2013.01); *C12P 19/12* (2013.01); *C12P 19/14* (2013.01); *C12Y 302/01091* (2013.01)

(58) Field of Classification Search
None
See application file for complete search history.

(56) References Cited

U.S. PATENT DOCUMENTS

| 9,963,692 B2 * | 5/2018 | Suda .................... C12N 9/2437 |
|---|---|---|
| 2015/0259660 A1 | 9/2015 | Okuma et al. |
| 2016/0053246 A1 | 2/2016 | Suda et al. |

FOREIGN PATENT DOCUMENTS

WO 2014/157492 A1 10/2014

OTHER PUBLICATIONS

UniProt Database Accession No. W4B4B2, Dec. 2015, 2 pages (Year: 2015).*
Boisset et al, "Imaging the Enzymatic Digestion of Bacterial Cellulose Ribbons Reveals the Endo Character of the Cellobiohydrolase Cel6A from Humicola insolens and Its Mode of Synergy with Cellobiohydrolase Cel7A", Applied and Environmental Microbiology, Apr. 2000, vol. 66, No. 4 p. 1444-1452.
Extended European Search Report dated Jul. 19, 2017 issued in the corresponding EP Patent Application 17161994.3.
Berger, E. et al., "Two noncellulosomal cellulases of Clostridium thermocellum, Cel91 and Ce148Y, hydrolyse arystalline cellulose synergistically: Clostridium thermocellum soluble synergistic cellulases", FEMS Microbiology Letters, vol. 268, No. 2, Jan. 24, 2007, pp. 194-201.
Database UniProt [Online] Oct. 1, 2002, "SubName:Full=Cellulose 1,4-beta-cellobiosidase {ECO:0000313IEMBL:CAD32945.1}; EC=3.2.1.91 {ECO:00003131EMBL:CAD32945.1};", XP002771733.
Voutilainen et al., "Cloning, expression, and characterization of novel thermostable family 7 cellobiohydrolases", Biotechnology and Bioengineering, Wiley ETC, vol. 101, No. 3, Oct. 1, 2008, pp. 515-528.

* cited by examiner

*Primary Examiner* — David Steadman
(74) *Attorney, Agent, or Firm* — Carrier Blackman & Associates, P.C.; Joseph P. Carrier; Fulchand P. Shende

(57) ABSTRACT

A thermostable cellobiohydrolase, having a cellobiohydrolase catalytic domain including: (A) a polypeptide including the amino acid sequence represented by SEQ ID NO: 1, (B) a polypeptide including an amino acid sequence in which at least one amino acid has been deleted, substituted, or added in the amino acid sequence represented by SEQ ID NO: 1, and having hydrolysis activity against a substrate of phosphoric acid swollen Avicel at least under conditions of 65° C. and pH 6, or (C) a polypeptide including an amino acid sequence having 80% or greater sequence identity with the amino acid sequence represented by SEQ ID NO: 1, and having hydrolysis activity against a substrate of phosphoric acid swollen Avicel at least under conditions of 65° C. and pH 6.

10 Claims, 5 Drawing Sheets

Specification includes a Sequence Listing.

FIG. 1

SEQUENCE LISTING

<160> NUMBER OF SEQ ID NOS: 8

<210> SEQ ID NO 1
<211> LENGTH: 784
<212> TYPE: PRT
<213> ORGANISM: Unknown
<220> FEATURE:
<223> OTHER INFORMATION: WN-12-A3-v6-4-10-11

<400> SEQUENCE: 1

```
Met Met Gln Gly Ile Val Arg Ser Ala Ser Arg Arg Ser Leu Ser Leu
1               5                   10                  15

Leu Leu Ala Val Ser Leu Ala Met Ala Ala Ile Ala Ser Leu Trp Ile
            20                  25                  30

Ala Pro Pro Gln Arg Ala Glu Ala Ala Ser Ile His Gln Gln Arg Phe
        35                  40                  45

Leu Gln Leu Tyr Asn Gln Ile Lys Asp Pro Ala Asn Gly Tyr Phe Ser
    50                  55                  60

Pro Glu Gly Ile Pro Tyr His Ala Val Glu Thr Leu Ile Ser Glu Ala
65                  70                  75                  80

Pro Asp Tyr Gly His Met Thr Thr Ser Glu Ala Tyr Ser Tyr Trp Leu
                85                  90                  95

Trp Leu Glu Thr Leu Tyr Gly Tyr Tyr Thr Gly Asp Trp Ser Arg Leu
            100                 105                 110

Glu Ala Ala Trp Asp Asn Met Glu Lys Tyr Ile Ile Pro Ile Asn Glu
        115                 120                 125

Gly Asp Gly Val Glu Glu Gln Pro Thr Met Asn Tyr Tyr Asn Pro Asn
    130                 135                 140

Ser Pro Ala Thr Tyr Ala Ala Glu His Pro Tyr Pro Asp Arg Tyr Pro
145                 150                 155                 160

Ser Glu Leu Ser Gly Gln Tyr Pro Ala Gly Arg Asp Pro Leu Asp Ala
                165                 170                 175

Glu Leu Lys Ala Thr Tyr Gly Asn Asn Gln Thr Tyr Leu Met His Trp
            180                 185                 190

Leu Leu Asp Val Asp Asn Trp Tyr Gly Phe Gly Asn Leu Leu Asn Pro
        195                 200                 205
```

Ser His Thr Ala Thr Tyr Val Asn Thr Phe Gln Arg Gly Glu Gln Glu
210                 215                 220

Ser Val Trp Glu Ala Ile Pro His Pro Ser Gln Asp Asp Lys Thr Phe
225                 230                 235                 240

Gly Lys Pro Asn Glu Gly Phe Met Ser Leu Phe Thr Lys Glu Asn Gln
                245                 250                 255

Ala Pro Ala Ala Gln Trp Arg Tyr Thr Ala Thr Asp Ala Asp Ala
        260                 265                 270

Arg Ala Val Gln Val Met Phe Trp Ala Gln Lys Leu Gly Tyr Asn Asn
                275                 280                 285

Pro Val Tyr Leu Asn Lys Ala Lys Lys Met Gly Asp Phe Leu Arg Tyr
290                 295                 300

Gly Met Tyr Asp Lys Tyr Phe Gln Gln Ile Gly Ser Ala Ser Asp Gly
305                 310                 315                 320

Ser Pro Thr Pro Gly Asn Gly Lys Asp Ala Ser Met Tyr Leu Leu Ala
                325                 330                 335

Trp Tyr Thr Ala Trp Gly Gly Leu Gly Pro Ser Gly Gln Trp Ala
                340                 345                 350

Trp Arg Ile Gly Ser Ser His Ala His Gln Ala Tyr Gln Asn Pro Val
                355                 360                 365

Ala Ala Tyr Ala Leu Ser Gln Pro Gly Gly Gly Leu Ile Pro Leu Ser
370                 375                 380

Pro Thr Ala Gln Ser Asp Trp Ala Gln Ser Leu Thr Arg Gln Leu Glu
385                 390                 395                 400

Phe Tyr Thr Trp Leu Gln Thr Ala Glu Gly Gly Ile Gly Gly Gly Ala
                405                 410                 415

Thr Asn Ser Trp Asn Gly Asp Tyr Ser Pro Tyr Pro Ala Gly Val Ser
                420                 425                 430

Thr Phe Tyr Gly Leu Ala Tyr Asp Glu Ala Pro Val Tyr His Asp Pro
                435                 440                 445

Asp Ser Asn Ser Trp Phe Gly Phe Gln Ala Trp Pro Met Glu Arg Val
                450                 455                 460

Ala Glu Leu Tyr Tyr Ile Leu Ala Gln Ser Gly Asp Thr Thr Ser Gln
465                 470                 475                 480

Asn Phe Gln Met Ala Lys Gln Val Ile Thr Lys Trp Ile Asp Trp Ser
                485                 490                 495

Met Asp Tyr Val Phe Ala Asn Glu Arg Pro Leu Thr Asp Asp Glu Gly
                500                 505                 510

Tyr Tyr Leu Asp Thr Ser Gly Arg Arg Ile Val Gly Gly Thr Asn Pro
                515                 520                 525

Ser Val Ala Thr Thr Pro Ala Pro Gly Glu Phe Trp Leu Pro Ser Thr
530                 535                 540

Leu Gly Trp Thr Gly Gln Pro Asp Pro Trp Arg Gly Phe Ala Ser Tyr
545                 550                 555                 560

Thr Gly Asn Pro Asn Tyr His Val Tyr Val Thr Asn Pro Ser Gln Asp
                565                 570                 575

Val Gly Val Leu Gly Ser Tyr Ile Lys Ala Leu Thr Phe Phe Ala Ala
                580                 585                 590

Gly Thr Arg Ala Glu Thr Gly Ser Tyr Thr Ala Leu Gly Asn Gln Ala
                595                 600                 605

Lys Asn Leu Ala Glu Glu Leu Leu Glu Val Ala Trp Asn Tyr Asn Asp
610                 615                 620

Gly Ile Gly Ile Ala Thr Pro Glu Pro Arg Glu Asp Tyr Tyr Arg Tyr

```
                625                 630                 635                 640

Phe Thr Lys Glu Ile Tyr Phe Pro Asn Gly Trp Ser Gly Thr Tyr Gly
                    645                 650                 655

Gln Gly Asn Thr Ile Pro Gly Asn Gly Val Pro Ser Asp Pro Ala
                    660                 665                 670

Lys Gly Gly Asn Gly Val Tyr Ile Ser Tyr Ala Glu Leu Arg Pro Lys
                    675                 680                 685

Ile Lys Gln Asp Pro Asn Trp Ala Tyr Leu Glu Asn Leu Tyr Leu Asn
                690                 695                 700

Ser Tyr Asn Pro Ala Thr Gly Lys Trp Glu Asn Gly Val Pro Thr Phe
    705                 710                 715                 720

Val Tyr His Arg Phe Trp Ala Gln Val Asp Met Ala Thr Ala Tyr Ala
                    725                 730                 735

Glu Phe Asp Arg Leu Ile Gly Ser Ser Ala Pro Thr Val Pro Ala Ala
                    740                 745                 750

Pro Thr Gly Leu Thr Ala Thr Ala Gly Asp Gly Gln Val Thr Leu Ala
                    755                 760                 765

Trp Asn Ala Ser Thr Ala Ala Thr Ser Tyr Thr Val Lys Arg Ala Thr
                770                 775                 780

<210> SEQ ID NO 2
<211> LENGTH: 2352
<212> TYPE: DNA
<213> ORGANISM: Unknown
<220> FEATURE:
<223> OTHER INFORMATION: WN-12-A3-v6-4-10-11

<400> SEQUENCE: 2
atgatgcagg gaatcgttcg atcggcttcg cggcggagcc tgtcgctcct tctcgccgtt      60
tcgctggcga tggccgcgat cgccagcctt tggatcgctc cccgcagcg ggcggaagcg      120 gcctcgattc atcaacagcg gtttctgcag ctttacaacc agatcaagga tccggccaac      180 ggctatttt cgccggaggg catcccttat acgccgtgg agacgctgat cagcgaagcg      240
ccggattacg ccacatgac cacttccgag gcgtacagct actggctatg gctgagacg      300 ctgtacggat actataccgg cgactggagc cggctgaaag cggcgtggga caacatggaa      360
aagtacatca ttccgatcaa cgagggagac ggcgtcgaag aacagccgac catgaactac      420
tacaatccga cagtccggc cacctacgcg gcggagcatc cgtatcccga ccgctatccc      480
tccgaactga cgggcaata tccggcggga cgggatccgc ttgacgccga gctgaaggcg      540
acctacggca caaccagac ctatctcatg cactggctgc tggatgtcga caactggtac      600
ggctttggca atctgctcaa cccgtcgcat acggccacgt acgtgaacac cttccaacgc      660
ggcgagcaag agtccgtgtg ggaagcgatc ccgcatccgt cgcaggatga caaaacgttc      720
ggcaaaccga cgaagggtt catgagcctg ttcaccaagg aaaaccaggc gccgccgcc      780 caatggcggt acaccgcggc gacgacgcc gacgcccggg ccgtccaggt catgttctgg      840
gcccagaagc tggggtataa caatccggtt tacctgaaca aggccaaaaa gatgggcgac      900 ttttgcgct acggcatgta tgacaagtat ttccaacaaa tcggcagcgc cagcgacggc      960
tcgcccacgc cgggcaacgg caaggacgcc agcatgtatt tgttggcctg gtacaccgcg     1020
tggggcggcg gtctcggtcc cagcggccaa tgggcgtggc gcatcggttc cagtcacgcg     1080
caccaggcgt accagaaccc ggtcgcggct tacgccctgt cccaacccgg cggcgggctg     1140
attccgctgt cgccgacggc ccagagcgac tgggcccaat cgctcacgcg ccaactggaa     1200
```

-continued

```
ttctacacct ggctgcagac ggcagaaggc ggaatcggcg gcggggcgac caacagttgg    1260
aacggggact acagtccgta ccccgcgggc gtcagcacgt tttacggtct ggcgtacgac    1320
gaggcgccgg tttaccacga cccggattcg aactcctggt tcgggttcca ggcgtggccg    1380
atggaacgcg tggccgagct ctactacatt ctcgcgcaaa gcggcgacac gacgtcgcaa    1440
aacttccaga tggccaagca ggtcatcacc aaatggatcg actggtcgat ggactatgtg    1500
ttcgccaatg agcgcccgtt gaccgacgat gaaggctact acctcgacac gtcgggacgg    1560
cggattgtcg gcggcacgaa tccgtcagtg gcgacgacgc ccgcgcccgg cgaattctgg    1620
cttccgagca cgctgggctg gaccgggcag ccggacccgt ggcgcgggtt tgcctcctat    1680
accggcaatc cgaattatca cgtgtacgtg acgaatccca gtcaggacgt cggcgtgctg    1740
ggcagctaca tcaaggcgct caccttcttt gcggccggaa cccgggccga aaccgggagc    1800
tataccgctc tgggcaacca ggcgaaaaat ctcgcggaag agctgctgga agtggcctgg    1860
aattacaacg acggcatcgg catcgcgacg ccggagcccc gtgaggacta ctatcgttat    1920
ttcaccaaag aaatttactt cccccaacggt tggagcggca cgtacggcca gggcaacacc    1980
attccgggca acggcggcgt tccgtccgat ccggccaaag gcggcaacgg cgtctacatc    2040
agctacgccg agcttcgtcc aaagatcaag caggacccga actgggcgta tctggaaaat    2100
ctttacctga actcttacaa cccggcgacg ggcaaatggg agaacggcgt gccgaccttc    2160
gtctaccacc gtttctgggc gcaagtggat atggccaccg catacgccga gttcgaccgg    2220
ttgatcggct cgtccgcacc gacggtgccg gcggcgccga cggggttgac cgccacggcg    2280
ggcgacggcc aggtgacgct cgcgtggaac gcctccaccg cagcgacgag ctacacggtg    2340
aagcgcgcca cc                                                        2352
```

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Primer.

<400> SEQUENCE: 3

```
atgatgcagg gaatcgttcg a                                                21
```

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Primer.

<400> SEQUENCE: 4

```
ggtggcgcgc ttcaccgtg                                                   19
```

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Primer.

<400> SEQUENCE: 5

```
gtgatgatgc agggaatcgt tcga                                             24
```

<210> SEQ ID NO 6
<211> LENGTH: 33

```
<212> TYPE: DNA
<213> ORGANISM: Artificial Sequence
<220> FEATURE:
<223> OTHER INFORMATION: Description of Artificial Sequence: Primer.

<400> SEQUENCE: 6
atgcaaagct tttaggtggc gcgcttcacc gtg                              33

<210> SEQ ID NO 7
<211> LENGTH: 1091
<212> TYPE: PRT
<213> ORGANISM: Paenibacillus sp. FSL H7-689

<400> SEQUENCE: 7
```

| Met | Leu | Lys | Ser | Ala | Ala | Lys | Lys | Ser | Leu | Thr | Ala | Met | Leu | Ala | Gly |
|---|---|---|---|---|---|---|---|---|---|---|---|---|---|---|---|
| 1 | | | | 5 | | | | | 10 | | | | | 15 | |

| Thr | Val | Met | Leu | Thr | Gly | Tyr | Thr | Gly | Leu | Trp | Ala | Gly | Pro | Gln | Thr |
|---|---|---|---|---|---|---|---|---|---|---|---|---|---|---|---|
| | | | 20 | | | | | 25 | | | | | 30 | | |

| Ala | His | Ala | Ala | Asp | Gln | Ala | Ile | Glu | Ile | Gln | Ala | Asp | Ser | Ile | Asn |
|---|---|---|---|---|---|---|---|---|---|---|---|---|---|---|---|
| | | 35 | | | | | 40 | | | | | 45 | | | |

| Glu | Ala | Arg | Phe | Leu | Gln | Leu | Tyr | Asp | Gln | Leu | Lys | Asp | Pro | Ala | Asn |
|---|---|---|---|---|---|---|---|---|---|---|---|---|---|---|---|
| | 50 | | | | | 55 | | | | | 60 | | | | |

| Gly | Tyr | Phe | Ser | Pro | Glu | Gly | Leu | Pro | Tyr | His | Ser | Ile | Glu | Thr | Leu |
|---|---|---|---|---|---|---|---|---|---|---|---|---|---|---|---|
| 65 | | | | | 70 | | | | | 75 | | | | | 80 |

| Leu | Ser | Glu | Ala | Pro | Asp | Tyr | Gly | His | Met | Thr | Thr | Ser | Glu | Ala | Tyr |
|---|---|---|---|---|---|---|---|---|---|---|---|---|---|---|---|
| | | | | 85 | | | | | 90 | | | | | 95 | |

| Ser | Tyr | Trp | Leu | Trp | Leu | Glu | Thr | Met | Tyr | Gly | His | Tyr | Thr | Gly | Asp |
|---|---|---|---|---|---|---|---|---|---|---|---|---|---|---|---|
| | | | 100 | | | | | 105 | | | | | 110 | | |

| Trp | Ser | Gln | Leu | Glu | Ala | Ala | Trp | Asp | Ser | Met | Glu | Lys | Tyr | Ile | Ile |
|---|---|---|---|---|---|---|---|---|---|---|---|---|---|---|---|
| | | 115 | | | | | 120 | | | | | 125 | | | |

| Pro | Val | Asn | Glu | Gly | Asp | Gly | Lys | Glu | Glu | Gln | Pro | Thr | Met | Ser | Ser |
|---|---|---|---|---|---|---|---|---|---|---|---|---|---|---|---|
| | 130 | | | | | 135 | | | | | 140 | | | | |

| Tyr | Asn | Pro | Asn | Ser | Pro | Ala | Thr | Tyr | Ala | Ala | Glu | Lys | Pro | Phe | Pro |
|---|---|---|---|---|---|---|---|---|---|---|---|---|---|---|---|
| 145 | | | | | 150 | | | | | 155 | | | | | 160 |

| Asp | Gln | Tyr | Pro | Ser | Gln | Leu | Asn | Gly | Gln | Tyr | Ala | Ala | Gly | Lys | Asp |
|---|---|---|---|---|---|---|---|---|---|---|---|---|---|---|---|
| | | | | 165 | | | | | 170 | | | | | 175 | |

| Pro | Ile | Asp | Ala | Glu | Leu | Lys | Ala | Thr | Tyr | Gly | Asp | Asn | Gln | Thr | Tyr |
|---|---|---|---|---|---|---|---|---|---|---|---|---|---|---|---|
| | | | 180 | | | | | 185 | | | | | 190 | | |

| Leu | Met | His | Trp | Leu | Val | Asp | Val | Asp | Trp | Tyr | Gly | Tyr | Gly | Asn |
|---|---|---|---|---|---|---|---|---|---|---|---|---|---|---|
| | | 195 | | | | | 200 | | | | | 205 | | |

| Leu | Leu | Asn | Pro | Ser | His | Thr | Ala | Thr | Tyr | Val | Asn | Thr | Phe | Gln | Arg |
|---|---|---|---|---|---|---|---|---|---|---|---|---|---|---|---|
| | 210 | | | | | 215 | | | | | 220 | | | | |

| Gly | Glu | Gln | Glu | Ser | Val | Trp | Glu | Ala | Ile | Pro | His | Pro | Ser | Gln | Asp |
|---|---|---|---|---|---|---|---|---|---|---|---|---|---|---|---|
| 225 | | | | | 230 | | | | | 235 | | | | | 240 |

| Asp | Lys | Ser | Phe | Gly | Lys | Ala | Asn | Glu | Gly | Phe | Met | Ser | Leu | Phe | Thr |
|---|---|---|---|---|---|---|---|---|---|---|---|---|---|---|---|
| | | | | 245 | | | | | 250 | | | | | 255 | |

| Lys | Glu | Asn | Gln | Val | Pro | Ser | Ala | Gln | Trp | Arg | Tyr | Thr | Asn | Ala | Thr |
|---|---|---|---|---|---|---|---|---|---|---|---|---|---|---|---|
| | | | 260 | | | | | 265 | | | | | 270 | | |

| Asp | Ala | Asp | Ala | Arg | Ala | Val | Gln | Val | Leu | Tyr | Trp | Ala | Lys | Glu | Met |
|---|---|---|---|---|---|---|---|---|---|---|---|---|---|---|---|
| | | 275 | | | | | 280 | | | | | 285 | | | |

| Gly | Tyr | Asn | Asn | Pro | Glu | Tyr | Leu | Asp | Lys | Ala | Lys | Lys | Met | Gly | Asp |
|---|---|---|---|---|---|---|---|---|---|---|---|---|---|---|---|
| | 290 | | | | | 295 | | | | | 300 | | | | |

| Tyr | Leu | Arg | Tyr | Gly | Met | Tyr | Asp | Lys | Tyr | Phe | Gln | Lys | Ile | Gly | Ser |
|---|---|---|---|---|---|---|---|---|---|---|---|---|---|---|---|
| 305 | | | | | 310 | | | | | 315 | | | | | 320 |

| Ala | Lys | Asn | Gly | Thr | Pro | Thr | Pro | Gly | Thr | Gly | Lys | Asp | Ser | Asn | Met |
|---|---|---|---|---|---|---|---|---|---|---|---|---|---|---|---|
| | | | | 325 | | | | | 330 | | | | | 335 | |

```
Tyr Leu Met Ala Trp Tyr Thr Ser Trp Gly Gly Leu Gly Gln Gly
            340                 345                 350

Gly Asp Trp Ala Trp Arg Ile Gly Ala Ser His Thr His Gln Ala Tyr
            355                 360                 365

Gln Asn Pro Val Ala Ala Tyr Ala Leu Ser Asp Pro Ala Gly Gly Leu
    370                 375                 380

Ile Pro Lys Ser Ala Thr Ala Lys Ala Asp Trp Asn Ala Thr Leu Lys
385                 390                 395                 400

Arg Gln Leu Glu Phe Tyr Thr Trp Leu Gln Ser His Glu Gly Ala Ile
            405                 410                 415

Gly Gly Gly Ala Thr Asn Ser Leu Asp Gly Ser Tyr Lys Ala Tyr Pro
            420                 425                 430

Ala Gly Val Ser Thr Phe Tyr Asp Met Ala Tyr Gln Glu Ala Pro Val
            435                 440                 445

Tyr Arg Asp Pro Asp Ser Asn Thr Trp Phe Gly Phe Gln Ala Trp Pro
450                 455                 460

Leu Glu Arg Val Ala Glu Met Tyr Tyr Ile Leu Ala Glu Ser Gly Asp
465                 470                 475                 480

Leu Thr Ser Glu Asn Phe Gln Met Ala Lys Lys Val Ile Thr Lys Trp
            485                 490                 495

Ile Asp Trp Ser Lys Asp Tyr Val Phe Val Gly Glu Arg Pro Val Thr
            500                 505                 510

Asp Ala Gln Gly Tyr Tyr Leu Asn Ala Ala Gly Gln Arg Ile Leu Gly
            515                 520                 525

Gly Thr Asn Val Gln Val Ala Thr Thr Pro Ala Pro Gly Glu Phe Trp
            530                 535                 540

Ile Pro Gly Gly Gln Glu Trp Gln Gly Gln Pro Asp Lys Trp Asn Gly
545                 550                 555                 560

Phe Ser Ser Phe Thr Glu Asn Pro Asn Phe Arg Val Thr Thr Lys Asp
            565                 570                 575

Pro Val Gln Asp Thr Gly Val Leu Gly Ser Tyr Val Lys Ala Leu Thr
            580                 585                 590

Phe Phe Ala Ala Gly Thr Gln Ala Glu Asn Gly Thr Leu Asn Ala Glu
            595                 600                 605

Gly Gln Glu Ala Lys Asp Leu Ala Glu Ala Leu Leu Asp Thr Ala Trp
            610                 615                 620

Asp Tyr Asn Asp Gly Val Gly Ile Val Thr Glu Glu Arg Lys Asp
625                 630                 635                 640

Tyr Phe Arg Phe Phe Ala Lys Glu Ile Tyr Ile Pro Ala Asn Trp Ser
            645                 650                 655

Gly Thr Phe Gly Gln Gly Asn Thr Ile Pro Gly Thr Ala Gly Val Pro
            660                 665                 670

Ser Asp Pro Ala Lys Gly Gly Asn Gly Val Tyr Ile Gly Tyr Ser Asp
            675                 680                 685

Leu Arg Pro Ala Ile Lys Gln Asp Pro Ala Trp Ala Tyr Leu Asp Asn
            690                 695                 700

Leu Tyr Lys Thr Ser Tyr Asn Pro Thr Thr Lys Gln Trp Glu Asn Gly
705                 710                 715                 720

Ala Pro Thr Phe Thr Tyr His Arg Phe Trp Ser Gln Val Asp Met Ala
            725                 730                 735

Thr Ala Tyr Gly Glu Tyr Asp Arg Leu Leu Gly Asp Ser Asp Ser Pro
            740                 745                 750
```

```
Glu Val Glu Val Pro Ala Ala Pro Ala Gly Val Thr Ala Thr Gly Gly
            755                 760                 765

Ser Glu Gln Val Val Leu Asn Trp Asn Ala Ala Gly Ala Ala Ser
    770                 775                 780

Tyr Thr Val Lys Arg Ala Glu Val Asn Gly Gly Pro Tyr Thr Ser Val
785                 790                 795                 800

Ala Thr Gly Val Thr Gly Ser Thr Phe Thr Asp Thr Gly Leu Thr Asn
                805                 810                 815

Gly Thr Thr Tyr Tyr Tyr Val Val Ala Val Asn Ala Val Gly Glu
                820                 825                 830

Ser Ala Pro Ser Thr Gln Ala Ser Ala Thr Pro Leu Ala Gly Thr Val
    835                 840                 845

Val Pro Gly Val Phe Asn Leu Thr Gly Thr Ala Gly Asp Ala Gln Ala
    850                 855                 860

Val Leu Thr Trp Thr Ala Ser Thr Gly Ala Ser Ser Tyr Lys Val Gln
865                 870                 875                 880

Arg Ser Val Gly Ser Gly Ala Tyr Ala Asp Leu Ala Thr Gly Leu Thr
                885                 890                 895

Ala Leu Thr Tyr Thr Asp Ala Thr Ala Val Asn Gly Thr Ala Tyr Asn
                900                 905                 910

Tyr Arg Val Val Ala Ser Asn Thr Ser Gly Gln Thr Asn Ser Asn Val
        915                 920                 925

Leu Val Leu Thr Pro Leu Ala Pro Pro Val Thr Thr Gly Thr Leu Glu
    930                 935                 940

Val Gln Tyr Arg Asn Gly Ser Ser Gly Thr Ser Val Asn Ala Ile Thr
945                 950                 955                 960

Pro Gln Phe Asn Val Lys Asn Thr Gly Thr Thr Ala Val Asp Leu Ser
                965                 970                 975

Lys Val Lys Val Arg Tyr Tyr Phe Thr Lys Asp Ser Ala Ala Asp Leu
                980                 985                 990

Ser Phe Trp Cys Asp Tyr Ala Gln Ile Gly Ser Gly Asn Val Glu Gly
            995                1000                1005

His Phe Val Ser Ile Asp Pro Ala Lys Gly Thr Ala Asp Thr Tyr
    1010                1015                1020

Leu Glu Ile Glu Phe Lys Ser Gly Ala Gly Ser Leu Ala Ala Gly
    1025                1030                1035

Ala Glu Thr Gly Ile Ile Gln Gly Arg Phe Ser Lys Asn Asn Trp
    1040                1045                1050

Thr Asn Phe Asp Gln Thr Asn Asp Tyr Ser Phe Asp Ser Thr Gln
    1055                1060                1065

Thr Ala Phe Ser Ala Trp Thr Lys Val Thr Ala Tyr Gln Asp Gly
    1070                1075                1080

Ala Lys Val Trp Gly Ile Glu Pro
    1085                1090

<210> SEQ ID NO 8
<211> LENGTH: 427
<212> TYPE: PRT
<213> ORGANISM: Unknown
<220> FEATURE:
<223> OTHER INFORMATION: AR19G-166RA

<400> SEQUENCE: 8

Leu Asp Asn Pro Phe Ile Gly Ala Ile Gly Tyr Val Asn Pro Asp Trp
1               5                   10                  15
```

```
Ala Thr Asn Val Ile Ser Gln Ala Asn Gln Thr Ala Asp Pro Thr Leu
            20                  25                  30

Ala Ala Gln Met Arg Lys Val Ala Thr Tyr Ser Thr Ala Val Trp Leu
        35                  40                  45

Asp Arg Ile Ala Ala Ile Thr Ala Gly Arg Gly Leu Arg Gly His Leu
    50                  55                  60

Asp Glu Ala Leu Arg Gln Met Gln Gln Ala Gly Gln Pro Val Val Ile
65                  70                  75                  80

Thr Leu Val Ile Tyr Asp Leu Pro Asn Arg Asp Cys Ser Ala Ala Ala
                85                  90                  95

Ser Asn Gly Glu Leu Leu Val Ala Gln Asn Gly Leu Ala Arg Tyr Lys
            100                 105                 110

Ala Glu Phe Ile Asp Pro Ile Val Ala Ile Leu Ser Asp Pro Arg Tyr
        115                 120                 125

Ala Gly Leu Arg Ile Val Thr Ile Ile Glu Pro Asp Ser Leu Pro Asn
    130                 135                 140

Leu Val Thr Asn Leu Ser Ile Pro Ala Cys Ala Glu Ala Gln Asn Ala
145                 150                 155                 160

Tyr Ile Glu Gly Ile Arg Tyr Ala Val Asn Arg Leu Arg Thr Ile Pro
                165                 170                 175

Asn Val Tyr Ile Tyr Leu Asp Ile Ala His Ser Gly Trp Leu Gly Trp
            180                 185                 190

Asp Asn Asn Phe Asn Gly Ala Val Asn Leu Tyr Thr Gln Val Val Gln
        195                 200                 205

Gly Met Asp Gln Gly Phe Asn Ser Ile Asp Gly Phe Ile Thr Asn Val
    210                 215                 220

Ala Asn Tyr Thr Pro Leu Glu Glu Pro Tyr Leu Pro Asp Pro Asn Leu
225                 230                 235                 240

Thr Ile Ala Gly Gln Pro Val Arg Ser Ala Ser Phe Tyr Glu Trp Asn
                245                 250                 255

Pro Tyr Phe Asp Glu Leu Asp Tyr Ala Leu Ala Leu Arg Asn Ala Phe
            260                 265                 270

Ile Gly Arg Gly Phe Pro Ser Thr Ile Gly Met Leu Ile Asp Thr Ser
        275                 280                 285

Arg Asn Gly Trp Gly Gly Cys Ser Tyr Gly Arg Cys Arg Pro Thr Gly
    290                 295                 300

Pro Ser Ser Asp Thr Ser Val Asn Ala Tyr Val Asp Gly Ser Arg
305                 310                 315                 320

Val Asp Arg Arg Tyr His Arg Gly Asn Trp Cys Asn Gln Ala Gly Gly
                325                 330                 335

Ile Gly Glu Arg Pro Gln Ala Ala Pro Arg Ser Gly Ile Asp Ala Tyr
            340                 345                 350

Val Trp Val Lys Pro Pro Gly Glu Ser Asp Gly Val Ser Gln Pro Gly
        355                 360                 365

Ile Val Asp Pro Asp Asp Pro Asn Lys Lys Phe Asp Pro Met Cys Asp
    370                 375                 380

Pro Asn Gly Gln Ser Arg Tyr Asn Ser Ala Tyr Pro Thr Gly Ala Leu
385                 390                 395                 400

Pro Asn Ala Pro His Ala Gly Arg Trp Phe Pro Gln Gln Phe Glu Ile
                405                 410                 415

Leu Val Arg Asn Ala Tyr Pro Pro Ile Gln Pro
            420                 425
```

THERMOSTABLE CELLOBIOHYDROLASE

TECHNICAL FIELD

The present invention relates to a thermostable cellobiohydrolase, a polynucleotide encoding the thermostable cellobiohydrolase, an expression vector for expressing the thermostable cellobiohydrolase, a transformant into which the expression vector has been incorporated, and a method for producing a cellulose degradation product using the thermostable cellobiohydrolase.

Priority is claimed on Japanese Unpublished Patent Application No. 2016-064525, filed Mar. 28, 2016, the content of which is incorporated herein by reference.

BACKGROUND ART

In recent years, as a result of environmental problems such as global warming and atmospheric pollution, as well as concerns related to energy supplies for transportation, including the dramatic increase in the cost of crude oil and the expectation of depletion of crude oil sources in the near future (peak oil), the development of alternative energy sources to oil has become an extremely important issue. Plant biomass or lignocellulose is the most plentiful renewable energy source on earth, and holds great promise as an alternative energy source to oil. The main component of plant biomass dry weight is lignocellulose, which is composed of polysaccharides such as cellulose and hemicellulose, and lignin. For example, polysaccharides can be hydrolyzed by a glycoside hydrolase such as a cellulase or hemicellulase to form monosaccharides such as glucose and xylose, which can then be used as biofuels or the raw materials for chemical products.

Lignocellulose is recalcitrant due to its highly complex structure, and is difficult to degrade or hydrolyze with a single glycoside hydrolase. The complete degradation of lignocellulose generally requires three types of enzymes, namely an endoglucanase (cellulase or endo-1,4-β-D-glucanase, EC 3.2.1.4), an exo-type cellobiohydrolase (1,4-β-cellobiosidase or cellobiohydrolase, EC 3.2.1.91, EC 3.2.1.176), and a β-glucosidase (EC 3.2.1.21), and it is thought that the addition of a further plurality of enzymes including the hemicellulase xylanase (endo-1,4-β-xylanase, EC 3.2.1.8) and other plant cell wall-degrading enzymes such as β-xylosidase (EC 3.2.1.37) is also necessary.

In conventional bioethanol production using lignocellulose as a starting resource, hydrolysis processes using high solid loading (30 to 60% solid loading) have been tested with the aim of achieving a more energy-efficient conversion to ethanol. However, in this type of lignocellulose enzymatic hydrolysis using high solid loading, the viscosity of the hydrolyzed biomass solution is high, and the hydrolysis reaction of the lignocellulose tends to proceed poorly. Accordingly, by using a thermostable enzyme and performing the enzymatic hydrolysis process at a high temperature, for example 65° C. or higher, the rate of the hydrolysis reaction can be increased, and the viscosity of the hydrolyzed biomass solution can be reduced, which is expected to enable a shortening of the hydrolysis reaction time and a reduction in the amount of enzyme required. As a result, for all of the various glycoside hydrolases, the development of enzymes having superior thermal stability is very desirable.

When cellulose is hydrolyzed by a cellobiohydrolase, the disaccharide cellobiose is the main product. Cellobiohydrolases include some types which initiate hydrolysis from the reducing ends of cellulose (such as cellobiohydrolases belonging to the GH7 and GH48 families and the like), and some types which initiate hydrolysis from the non-reducing ends (such as cellobiohydrolases belonging to the GH15, GH16 and GH9 families and the like), and it is known that if the two types are used in combination, then the cellulose degradation activity is superior to that when either type is used alone (for example, see Non-Patent Document 1). Among cellobiohydrolases which initiate hydrolysis from the non-reducing ends of cellulose, a cellobiohydrolase of the GH6 family having an optimum temperature exceeding 75° C. has been reported (for example, see Patent Document 1).

PRIOR ART LITERATURE

Patent Documents

Patent Document 1: International Patent Publication No. 2014/157492

Non-Patent Documents

Non-Patent Document 1: Boisset et al., Applied and Environmental Microbiology, 2000, vol. 66, pp. 1444 to 1452.

SUMMARY OF THE INVENTION

Problems to be Solved by the Invention

The present invention has an object of providing a novel thermostable cellobiohydrolase belonging to the GH48 family, which exhibits cellobiohydrolase activity at least at 65° C., and at 70° C. in the presence of calcium ions, and also exhibits a synergistic effect with cellobiohydrolases of the GH6 family, as well as providing a polynucleotide encoding the thermostable cellobiohydrolase, an expression vector for expressing the thermostable cellobiohydrolase, a transformant into which the expression vector has been incorporated, and a method for producing a cellulose degradation product using the thermostable cellobiohydrolase.

Means for Solving the Problem

In order to achieve the above object, the inventors of the present invention extracted DNA directly from a compost culture, and by carrying out large-scale genomic sequencing of the microbial flora that was difficult to isolate, they succeeded in obtaining a thermostable cellobiohydrolase having a novel amino acid sequence, thus enabling them to complete the present invention.

In other words, a thermostable cellobiohydrolase, a polynucleotide, an expression vector, a transformant, a method for producing a thermostable cellobiohydrolase, a cellulase mixture, and a method for producing a cellulose degradation product according to the present invention have the aspects [1] to [12] described below.

[1] A thermostable cellobiohydrolase, having a cellobiohydrolase catalytic domain including:

(A) a polypeptide including the amino acid sequence represented by SEQ ID NO: 1, (B) a polypeptide including an amino acid sequence in which at least one amino acid has been deleted, substituted, or added in the amino acid sequence represented by SEQ ID NO: 1, and having hydrolysis activity against a substrate of phosphoric acid swollen Avicel at least under conditions of 65° C. and pH 6, or (C) a polypeptide including an amino acid sequence having 80% or greater sequence identity with the amino acid sequence represented by SEQ ID NO: 1, and having hydrolysis activity against a substrate of phosphoric acid swollen Avicel at least under conditions of 65° C. and pH 6.

[2] The thermostable cellobiohydrolase according to [1] which, in the presence of calcium ions, exhibits hydrolysis activity against a substrate of phosphoric acid swollen Avicel at least under conditions of 70° C. and pH 6.

[3] A polynucleotide, having a region encoding a cellobiohydrolase catalytic domain, the region including:

(a) a nucleotide sequence encoding a polypeptide including the amino acid sequence represented by SEQ ID NO: 1, (b) a nucleotide sequence encoding a polypeptide which includes an amino acid sequence in which at least one amino acid has been deleted, substituted, or added in the amino acid sequence represented by SEQ ID NO: 1, and has hydrolysis activity against a substrate of phosphoric acid swollen Avicel at least under conditions of 65° C. and pH 6, (c) a nucleotide sequence encoding a polypeptide which includes an amino acid sequence having 80% or greater sequence identity with the amino acid sequence represented by SEQ ID NO: 1, and has hydrolysis activity against a substrate of phosphoric acid swollen Avicel at least under conditions of 65° C. and pH 6, (d) a nucleotide sequence having 80% or greater sequence identity with a nucleotide sequence represented by SEQ ID NO: 2, and encoding a polypeptide that has hydrolysis activity against a substrate of phosphoric acid swollen Avicel at least under conditions of 65° C. and pH 6, or (e) a nucleotide sequence of a polynucleotide which hybridizes under stringent conditions with a polynucleotide including the nucleotide sequence represented by SEQ ID NO: 2, the nucleotide sequence encoding a polypeptide having hydrolysis activity against a substrate of phosphoric acid swollen Avicel at least under conditions of 65° C. and pH 6.

[4] The polynucleotide according to [3], wherein the polypeptide also exhibits, in the presence of calcium ions, hydrolysis activity against a substrate of phosphoric acid swollen Avicel at least under conditions of 70° C. and pH 6.

[5] An expression vector incorporating the polynucleotide according to [3] or [4], the expression vector being capable of expressing a polypeptide having cellobiohydrolase activity in a host cell.

[6] A transformant into which the expression vector according to [5] has been introduced.

[7] The transformant according to [6], which is a eukaryote.

[8] A method for producing a thermostable cellobiohydrolase, the method including generating the thermostable cellobiohydrolase in the transformant according to [6] or [7].

[9] A glycoside hydrolase mixture, including the thermostable cellobiohydrolase according to [1] or [2], a thermostable cellobiohydrolase encoded by the polynucleotide according to [3] or [4], or a thermostable cellobiohydrolase produced by the method for producing a thermostable cellobiohydrolase according to [8], and at least one other glycoside hydrolase.

[10] The glycoside hydrolase mixture according to [9], also including a GH6 family cellobiohydrolase.

[11] A method for producing a cellulose degradation product, the method including generating the cellulose degradation product by bringing a material containing cellulose into contact with the thermostable cellobiohydrolase according to [1] or [2], a thermostable cellobiohydrolase encoded by the polynucleotide according to [3] or [4], the transformant according to [6] or [7], a thermostable cellobiohydrolase produced by the method for producing a thermostable cellobiohydrolase according to [8], or the glycoside hydrolase mixture according to [9].

[12] The method for producing a cellulose degradation product according to [11], wherein the material containing cellulose is brought into contact with the thermostable cellobiohydrolase or the glycoside hydrolase mixture, and with a GH6 family cellobiohydrolase.

Effects of the Invention

The thermostable cellobiohydrolase according to the present invention has cellobiohydrolase activity at least at 65° C. and pH 6, and at least at 70° C. and pH 6 in the presence of calcium ions. Moreover, the cellobiohydrolase activity of the thermostable cellobiohydrolase according to the present invention exhibits a synergistic effect with cellobiohydrolases of the GH6 family. For this reason, the thermostable cellobiohydrolase is suitable for hydrolysis processes of cellulose under high-temperature conditions.

Furthermore, the polynucleotide according to the present invention, an expression vector incorporating the polynucleotide, and a transformant into which the expression vector has been introduced can be used favorably in the production of the thermostable cellobiohydrolase according to the present invention.

BRIEF DESCRIPTION OF THE DRAWINGS

FIG. 1 is an alignment diagram of the amino acid sequence (SEQ ID NO: 1) of a polypeptide presumed to be encoded by an open reading frame WN12-A3-v6-4 and the amino acid sequence (SEQ ID NO: 7) of a cellulose 1,4-β-cellobiosidase of *Paenibacillus* subsp. FSL H7-689.

DETAILED DESCRIPTION OF THE INVENTION

[Thermostable Cellobiohydrolase]

Figure 2:
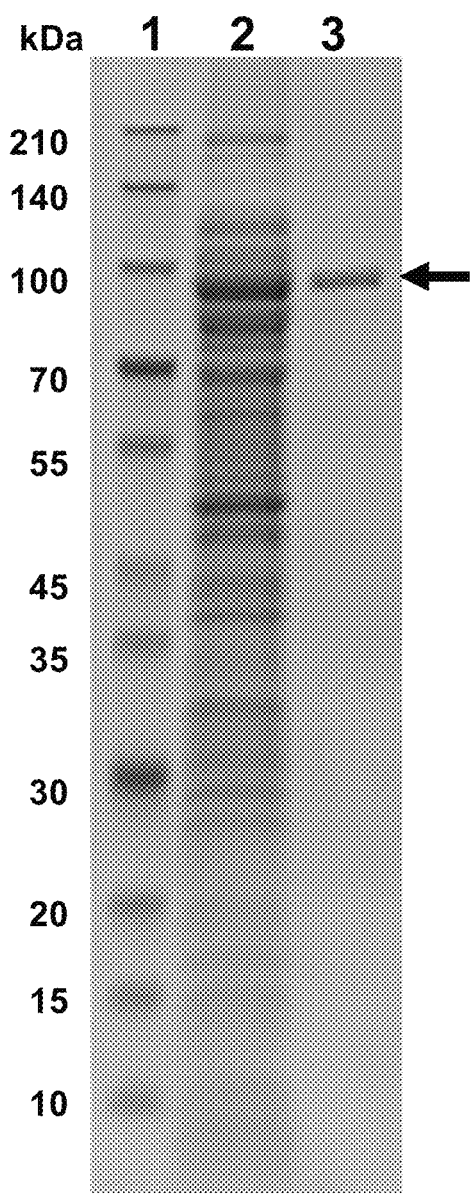
FIG. 2 is a diagram showing the SDS-PAGE analysis results of the WN12-A3-v6-4-10-11 protein obtained by expressing the WN12-A3-v6-4-10-11 gene in *E. coli* in Example 1.

Many microorganisms including filamentous fungi, bacteria and Archaea are difficult to culture, and it is said that about 99% of the microorganisms inhabiting microbial environments such as soil are still unknown. In particular, the culturing of microorganisms that exist in high-temperature environments is extremely difficult, and it is thought that using current culturing techniques that target the isolation of microorganisms, a mere 0.1% or less of the microorganisms that exist in natural samples extracted from the natural world have been able to be isolated. This difficulty in culturing microorganisms is one of the reasons hindering the development of thermostable cellobiohydrolases. Accordingly, the development of thermostable cellobiohydrolases requires an approach that does not rely on conventional isolation and culturing techniques.

In recent years, as a result of the development of next generation sequencers that enable a large amount of sequencing of giga base pairs, whole genome sequencing of the microbial flora contained in soils or the like has become possible. By using this analysis technology, the metagenomic analysis method has been proposed, in which the genomic DNA of a microbial group is prepared from an environmental sample such as soil, the genomes of the group having non-uniform and miscellaneous genomic compositions are sequenced directly and comprehensively, and the sequenced data are assembled by a parallel computer, thereby reconstructing the genomic sequences of the microbial flora. This method has contributed to rapid progress in the genome sequencing of microorganisms that are difficult to culture. However, in compost samples, where the decomposition of organic matter is proceeding vigorously, a multitude of microorganisms exist, and even if a next generation sequencer is used, a larger amount of sequencing is still required to comprehensively sequence the genome. Accordingly, in order to more efficiently obtain the microbial flora having the targeted properties, the inventors of the present invention have used a technique in which culturing is performed in a medium that uses only cellulose as a carbon source.

As shown in Example 1 described below, the inventors of the present invention extracted the genomic DNA (metagenomic DNA) of microbial groups from compost cultures collected from locations in Japan, and conducted shotgun sequencing and annotation of the metagenomic DNA, thus obtaining open reading frames (ORFs) encoding amino acid sequences similar to those of known cellobiohydrolases (for example, amino acid sequences having 20% or higher sequence identity, and an expectation value (E-value) of less than $1e^{-20}$). Primers were then designed based on the nucleotide sequence information of the obtained ORFs, and gene candidates were cloned from the genomic DNA of the compost cultures by the PCR method. The PCR-cloned DNAs were incorporated into *E. coli*, and proteins encoded by these nucleotide sequences were expressed and subjected to functional screening by phosphoric acid swollen Avicel (hereafter sometimes abbreviated as PSA) degradation activity assay. Finally, a thermostable cellobiohydrolase (hereafter sometimes referred to as "WN12-A3-v6-4-10-11" or the "gene clone WN12-A3-v6-4-10-11") having PSA degradation activity was obtained from these ORFs. The amino acid sequence of WN12-A3-v6-4-10-11 is represented by SEQ ID NO: 1, and the nucleotide sequence encoding the amino acid sequence of WN12-A3-v6-4-10-11 is represented by SEQ ID NO: 2.

As shown below in Example 1, WN12-A3-v6-4-10-11 exhibits a high level of hydrolysis activity against PSA, and also exhibits slight hydrolysis activity against crystalline cellulose Avicel and lichenan, which is composed of glucans having β-1,3 linkages and β-1,4 linkages, but exhibits almost no hydrolysis activity against carboxymethyl cellulose (hereafter sometimes abbreviated as CMC), laminarin, xylan, p-nitrophenyl-β-D-glucopyranoside (hereafter sometimes abbreviated as PNPG), and p-nitrophenyl-β-D-cellobioside (hereafter sometimes abbreviated as PNPC). This substrate specificity suggests that WN12-A3-v6-4-10-11 is a glycoside hydrolase having cellobiohydrolase activity.

In the present description, the expression "cellobiohydrolase activity" means enzymatic activity which promotes the hydrolysis of materials containing compounds having β-glycosidic linkages, and for example, means activity which produces cellobiose when a compound having β-glycosidic linkages such as PSA is used as a substrate, and the substrate is subjected to hydrolysis. Examples of the "compound having β-glycosidic linkages" include glucans having β-glycosidic linkages and oligosaccharides having β-glycosidic linkages.

Further, in the present description, the expression "has activity" means that the enzyme acts against at least one substrate, with a significant difference occurring in the amount of reducing ends or the color development reaction of the hydrolyzed substrate compared with a negative control.

Accordingly, the expression "has cellobiohydrolase activity" means that the enzyme acts against at least PSA, and generates a significant difference in the amount of reducing ends or the color development reaction of the hydrolyzed substrate compared with a negative control.

When the amino acid sequence of WN12-A3-v6-4-10-11 was searched against a database of known amino acid sequences, the amino acid sequence that showed the highest sequence identity was that of a cellulose 1,4-β-cellobiosidase belonging to the GH family 48 of *Paenibacillus* subsp. FSL H7-689 (SEQ ID NO: 7), and the sequence identity (homology) in the GH48 catalytic domain was 77%. Based on the substrate specificity and the sequence identity of the amino acid sequence with that of known cellobiohydrolases, it was clear that WN12-A3-v6-4-10-11 was a novel cellobiohydrolase belonging to the GH48 family.

WN12-A3-v6-4-10-11 has activity against a PSA substrate (namely, cellobiohydrolase activity) at least under conditions of 65° C. and pH 6.

Actually, as shown below in Example 1, WN12-A3-v6-4-10-11 exhibits cellobiohydrolase activity within a temperature range from 50 to 70° C., and across a pH range from 5.5 to 8. More specifically, the cellobiohydrolase activity of WN12-A3-v6-4-10-11 increases with increasing temperature within a range from 50 to 65° C., but then tends to decrease rapidly above 65° C.

Further, in the presence of divalent metal ions, WN12-A3-v6-4-10-11 exhibits high cellobiohydrolase activity at even higher temperatures than those observed in the absence of such metal ions. Actually, as shown below in Example 1, in the presence of calcium ions, WN12-A3-v6-4-10-11 exhibits cellobiohydrolase activity within a temperature range from 55 to 75° C. and across a broad pH range from 5.5 to 8.

Generally, in a protein having some form of bioactivity, one or more amino acids can be deleted, substituted, or added, without impairing the bioactivity. In other words, in WN12-A3-v6-4-10-11, one or more amino acids can be deleted, substituted, or added without impairing the cellobiohydrolase activity.

Hence, the thermostable cellobiohydrolase according to the present invention is a thermostable cellobiohydrolase having a cellobiohydrolase catalytic domain including any of the following (A) to (C):

(A) a polypeptide including the amino acid sequence represented by SEQ ID NO: 1, (B) a polypeptide including an amino acid sequence in which at least one amino acid has been deleted, substituted, or added in the amino acid sequence represented by SEQ ID NO: 1, and having hydrolysis activity against a substrate of PSA at least under conditions of 65° C. and pH 6, or (C) a polypeptide including an amino acid sequence having 80% or greater sequence identity with the amino acid sequence represented by SEQ ID NO: 1, and having hydrolysis activity against a substrate of PSA at least under conditions of 65° C. and pH 6.

In the above polypeptide of (B), the number of amino acids deleted, substituted, or added in the amino acid sequence represented by SEQ ID NO: 1 is preferably 1 to 20, more preferably 1 to 10, and still more preferably 1 to 5.

In the present description, a "polypeptide in which an amino acid is deleted" means a polypeptide in which a portion of the amino acids that constitute the polypeptide is missing (removed).

In the present description, a "polypeptide in which an amino acid is substituted" means a polypeptide in which an amino acid that constitutes the polypeptide has been replaced with a different amino acid.

In the present description, a "polypeptide in which an amino acid is added" means a polypeptide in which a new amino acid has been inserted within the polypeptide.

In the above polypeptide of (C), the sequence identity with the amino acid sequence represented by SEQ ID NO: 1 is not specifically limited as long as it is 80% or greater but less than 100%, but the sequence identity is preferably 85% or greater but less than 100%, more preferably 90% or greater but less than 100%, still more preferably 95% or greater but less than 100%, and most preferably 98% or greater but less than 100%.

The sequence identity (homology) between a pair of amino acid sequences is determined by juxtaposing the two amino acid sequences, while inserting gaps in some parts of the sequences to account for insertions and deletions, so as to achieve the best match between corresponding amino acids, and then calculating the proportion of matched amino acids relative to the whole amino acid sequences, excluding gaps, in the resulting alignment. The sequence identity between a pair of amino acid sequences can be determined using a variety of homology search software well known in the art. The sequence identity values between amino acid sequences in the present invention were obtained by calculation on the basis of an alignment obtained from the publicly known homology search software BLASTP.

The aforementioned polypeptides of (B) and (C) may be artificially designed, or may be homologs of WN12-A3-v6-4-10-11 or the like, or partial proteins thereof.

Each of the aforementioned polypeptides of (A) to (C) may be chemically synthesized based on the amino acid sequence, or may be generated by a protein expression system using the polynucleotide according to the present invention described below. Further, each of the polypeptides of (B) and (C) can also be artificially synthesized based on the polypeptide including the amino acid sequence represented by SEQ ID NO: 1, by using a gene recombination technique to introduce one or more amino acid mutations.

Each of the polypeptides of (A) to (C) has activity against a PSA substrate (cellobiohydrolase activity) at least under conditions of 65° C. and pH 6. As a result, a thermostable cellobiohydrolase can be obtained by having any of the polypeptides of (A) to (C) as the cellobiohydrolase catalytic domain.

The thermostable cellobiohydrolase according to the present invention acts against PSA as a substrate. The thermostable cellobiohydrolase may also act against other β-glucans or oligosaccharides besides PSA as substrates. Examples of these other β-glucans or oligosaccharides include crystalline celluloses such as Avicel, bacterial microcrystalline cellulose (hereafter sometimes abbreviated as BMCC) and filter paper; CMC; glucans composed of β-1,4 linkages; oligosaccharides composed of β-1,4 linkages such as cellobiose; xylan, p-nitrophenyl-β-D-galactopyranoside (hereafter sometimes abbreviated as PNPGAL); p-nitrophenyl-β-D-xylopyranoside (hereafter sometimes abbreviated as PNPX); glucans composed of β-1,3 and β-1,4 linkages such as lichenan; glucans composed of β-1,3 and β-1,6 linkages such as laminarin; glucans composed of β-1,3 linkages; glucans composed of β-1,6 linkages; and oligosaccharides composed of β-1,6 linkages such as gentiobiose. The thermostable cellobiohydrolase according to the present invention preferably acts against Avicel and lichenan substrates in addition to PSA.

The thermostable cellobiohydrolase according to the present invention exhibits hydrolysis activity (cellobiohydrolase activity) against a PSA substrate, at least under conditions of pH 6, preferably within a temperature range from 60 to 65° C., more preferably within a temperature range from 55 to 65° C., and still more preferably within a temperature range from 55 to 70° C. The optimum temperature of the thermostable cellobiohydrolase according to the present invention is preferably within a range from 60 to 70° C.

The term "thermostable" used in relation to the thermostable cellobiohydrolase according to the present invention means the cellobiohydrolase has cellobiohydrolase activity within a temperature range from 50 to 70° C.

The optimum pH of the thermostable cellobiohydrolase according to the present invention is within a range from pH 5.5 to 6.5. The thermostable cellobiohydrolase according to the present invention preferably exhibits cellobiohydrolase activity at least within a range from pH 5.5 to 7.0.

In the presence of divalent metal ions, one aspect of the thermostable cellobiohydrolase according to the present invention preferably exhibits superior cellobiohydrolase activity at even higher temperatures than those observed in the absence of such metal ions.

In the presence of divalent metal ions, the thermostable cellobiohydrolase according to the present invention preferably has cellobiohydrolase activity at least under conditions of 70° C. and pH 6, more preferably exhibits cellobiohydrolase activity across a temperature range from 65 to 75° C., and across a pH range from 5.5 to 7.0, and still more preferably exhibits cellobiohydrolase activity across a temperature range from 55 to 75° C., and across a pH range from 5.5 to 7.0.

The thermostable cellobiohydrolase according to the present invention may also have other cellulose hydrolysis activity besides the cellobiohydrolase activity. Examples of this other cellulose hydrolysis activity include xylanase activity, β-galactosidase activity, endoglucanase activity, xylosidase activity or β-glucosidase activity.

The thermostable cellobiohydrolase according to the present invention may be an enzyme composed solely of the cellobiohydrolase catalytic domain including any of the aforementioned polypeptides of (A) to (C), or may be an enzyme that also includes other domains in addition to the cellobiohydrolase catalytic domain. Examples of these other domains include other domains of conventionally known cellobiohydrolases besides the enzyme catalytic domain. For example, the thermostable cellobiohydrolase according to the present invention also includes enzymes obtained by substituting the enzyme catalytic domain in a publicly known cellobiohydrolase with any of the aforementioned polypeptides of (A) to (C).

When the thermostable cellobiohydrolase according to the present invention includes one or more other domains besides the cellobiohydrolase catalytic domain, the thermostable cellobiohydrolase preferably includes a cellulose-binding module (hereafter sometimes abbreviated as CBM). The cellulose-binding module may be positioned upstream (on the N-terminal side) or downstream (on the C-terminal side) of the cellobiohydrolase catalytic domain. Further, the cellulose-binding module and the cellobiohydrolase catalytic domain may be either bonded directly or bonded via a linker region of appropriate length. In the thermostable cellobiohydrolase according to the present invention, a cellulose-binding module preferably exists either upstream or downstream from the cellobiohydrolase catalytic domain with a linker region positioned therebetween, and a thermostable cellobiohydrolase in which a cellulose-binding module exists upstream of the cellobiohydrolase catalytic domain with a linker region positioned therebetween is particularly preferred.

The cellulose binding module included in the thermostable cellobiohydrolase according to the present invention is a region having the ability to bind cellulose, such as the ability to bind PSA or crystalline Avicel, and there are no particular limitations on the amino acid sequence of the module. Examples of this cellulose-binding module include the types of cellulose-binding modules present in known proteins, and appropriately modified versions thereof. Further, in those cases where the thermostable cellobiohydrolase according to the present invention includes both the cellobiohydrolase catalytic domain and a cellulose-binding module, it is preferable that these two are bonded via a linker sequence. There are no particular limitations on the amino acid sequence or the length and the like of the linker sequence.

The thermostable cellobiohydrolase according to the present invention may also have, at either the N-terminal or the C-terminal, a signal peptide capable of migration to and localization within a specific region within a cell, or a signal peptide that causes secretion from a cell. Examples of these types of signal peptides include apoplastic transport signal peptides, endoplasmic reticulum retention signal peptides, nuclear transport signal peptides, and secretory signal peptides. Specific examples of the endoplasmic reticulum retention signal peptides include signal peptides including an HDEL amino acid sequence.

Furthermore, the thermostable cellobiohydrolase according to the present invention may also have various types of tags added, for example at the N-terminal or the C-terminal, so as to facilitate easy purification in the case of generation using an expression system. Examples of tags that may be used include the types of tags widely used in the expression or purification of recombinant proteins, such as His tags, HA (hemagglutinin) tags, Myc tags and Flag tags.

In other words, one aspect of the thermostable cellobiohydrolase according to the present invention contains a cellobiohydrolase catalytic domain including any of the aforementioned polypeptides of (A) to (C); and also contains, according to need, at least one moiety selected from the group consisting of a cellulose-binding module positioned either upstream or downstream of the cellobiohydrolase catalytic domain, a linker region, a signal peptide added to either the N-terminal or the C-terminal of the thermostable cellobiohydrolase, and a tag added to either the N-terminal or the C-terminal of the thermostable cellobiohydrolase.

[Polynucleotide Encoding Thermostable Cellobiohydrolase]

The polynucleotide according to the present invention encodes the thermostable cellobiohydrolase according to the present invention. By introducing an expression vector incorporating the polynucleotide into a host, the thermostable cellobiohydrolase described above can be produced by using the expression system of the host.

Specifically, the polynucleotide according to the present invention is a polynucleotide having a region encoding a cellobiohydrolase catalytic domain, the region including any of the following nucleotide sequences (a) to (e):

(a) a nucleotide sequence encoding a polypeptide including the amino acid sequence represented by SEQ ID NO: 1, (b) a nucleotide sequence encoding a polypeptide which includes an amino acid sequence in which at least one amino acid has been deleted, substituted, or added in the amino acid sequence represented by SEQ ID NO: 1, and has hydrolysis activity against a substrate of PSA at least under conditions of 65° C. and pH 6, (c) a nucleotide sequence encoding a polypeptide which includes an amino acid sequence having 80% or greater sequence identity with the amino acid sequence represented by SEQ ID NO: 1, and has hydrolysis activity against a substrate of PSA at least under conditions of 65° C. and pH 6, (d) a nucleotide sequence having 80% or greater sequence identity with a nucleotide sequence represented by SEQ ID NO: 2, and encoding a polypeptide that has hydrolysis activity against a substrate of PSA at least under conditions of 65° C. and pH 6, or (e) a nucleotide sequence of a polynucleotide which hybridizes under stringent conditions with a polynucleotide including the nucleotide sequence represented by SEQ ID NO: 2, the nucleotide sequence encoding a polypeptide having hydrolysis activity against a substrate of PSA at least under conditions of 65° C. and pH 6.

In the present description, a "polynucleotide in which a nucleotide is deleted" means a polynucleotide in which a portion of the nucleotides that constitute the polynucleotide is missing (removed).

In the present description, a "polynucleotide in which a nucleotide is substituted" means a polynucleotide in which a nucleotide that constitutes the polynucleotide has been replaced with a different nucleotide.

In the present description, a "polynucleotide in which a nucleotide is added" means a polynucleotide in which a new nucleotide has been inserted within the polynucleotide.

In the present description, the expression "stringent conditions" can be exemplified by the method disclosed in Molecular Cloning: A Laboratory Manual, Third Edition (Sambrook et al., Cold Spring Harbor Laboratory Press). This example includes conditions in which hybridization is performed by incubation in a hybridization buffer composed of 6×SSC (composition of 20×SSC: 3 M sodium chloride, 0.3 M citric acid solution, pH 7.0), 5×Denhardt's solution (composition of 100×Denhardt's solution: 2% by mass of bovine serum albumin. 2% by mass of Ficoll, 2% by mass of polyvinylpyrrolidone), 0.5% by mass of SDS, 0.1 mg/ml, of salmon sperm DNA, and 50% formamide, at a temperature of 42 to 70° C. for several hours to overnight. The washing buffer used in the washing that is performed after the incubation is preferably a 1×SSC solution containing 0.1% by mass of SDS, and is more preferably a 0.1×SSC solution containing 0.1% by mass of SDS.

In the aforementioned nucleotide sequences of (a) to (e), it is preferable to select a degenerate codon having a high frequency of usage in the host. For example, the aforementioned nucleotide sequence of (a) may be either the nucleotide sequence represented by SEQ ID NO: 2, or a nucleotide sequence obtained by modifying the nucleotide sequence represented by SEQ ID NO: 2 to codons having a higher frequency of usage in the host without changing the amino acid sequence encoded by the nucleotide sequence. This codon modification can be achieved using a known gene sequence variation technique or artificial gene synthesis.

The polynucleotide including the nucleotide sequence represented by SEQ ID NO: 2 may be chemically synthesized based on the nucleotide sequence information, or may be obtained from the natural world using gene recombination techniques as either a full-length gene that encodes WN12-A3-v6-4-10-11 (hereafter sometimes referred to as the "WN12-A3-v6-4-10-11 gene") or a partial region thereof including the cellobiohydrolase catalytic domain. The full length of the WN12-A3-v6-4-10-11 gene or the partial region thereof can be obtained, for example, by collecting a sample containing microorganisms from the natural world, and conducting PCR using a genomic DNA recovered from the sample as a template, with a forward primer and a reverse primer designed by normal methods based on the nucleotide sequence represented by SEQ ID NO: 2. The cDNA synthesized by a reverse transcription reaction using mRNA recovered from the sample as a template may also be used as a template.

In the aforementioned nucleotide sequence of (d), the sequence identity with the nucleotide sequence represented by SEQ ID NO: 2 is not specifically limited as long as it is 80% or greater but less than 100%, but the sequence identity is preferably 85% or greater but less than 100%, more preferably 90% or greater but less than 100%, still more preferably 95% or greater but less than 100%, and most preferably 98% or greater but less than 100%.

The sequence identity (homology) between a pair of nucleotide sequences is determined by juxtaposing the two nucleotide sequences, while inserting gaps in some parts of the sequences to account for insertions and deletions, so as to achieve the best match between corresponding nucleotides, and then calculating the proportion of matched nucleotides relative to the whole nucleotide sequences, excluding gaps, in the resulting alignment. The sequence identity between a pair of nucleotide sequences can be determined using a variety of homology search software well known in the art. The sequence identity values between nucleotide sequences in the present invention were obtained by calculation on the basis of an alignment obtained from the publicly known homology search software BLASTN.

For example, each of the polynucleotides including an aforementioned nucleotide sequence of (b), (c) or (d) can be artificially synthesized by deleting, substituting, or adding one or a plurality of nucleotides in a polynucleotide including the nucleotide sequence represented by SEQ ID NO: 2.

Further, the nucleotide sequence of (b), (c) or (d) may also be a full-length sequence of a homologous gene of the WN12-A3-v6-4-10-11 gene or a partial sequence thereof. The homologous gene of the WN12-A3-v6-4-10-11 gene can be obtained by a gene recombination technique used in obtaining homologous genes of a gene for which the nucleotide sequence is already known.

The polynucleotide according to the present invention may have only the region encoding the cellobiohydrolase catalytic domain, or may also have, in addition to this region, one or more other regions encoding a cellulose-binding module, a linker sequence, various types of signal peptides, or various types of tags or the like.

In other words, one aspect of the polynucleotide according to the present invention contains a region encoding a cellobiohydrolase catalytic domain, the region including one of the aforementioned nucleotide sequences of (a) to (e), and also contains, according to need, a region encoding at least one moiety selected from the group consisting of a cellulose-binding module, a linker sequence, a signal peptide and a tag.

[Expression Vector]

The expression vector according to the present invention incorporates the aforementioned polynucleotide according to the present invention, and is capable of expressing, in a host cell, a polypeptide having cellobiohydrolase activity at least under conditions of 65° C. and pH 6. In other words, the expression vector of the present invention is an expression vector into which the polynucleotide according to the present invention has been incorporated in a state capable of expressing the thermostable cellobiohydrolase according to the present invention. More specifically, an expression cassette composed of, in order from the upstream side, DNA having a promoter sequence, the aforementioned polynucleotide according to the present invention and DNA having a terminator sequence, must be incorporated into the expression vector. Incorporation of the polynucleotide into the expression vector can be achieved using known gene recombination techniques, or a commercially available expression vector preparation kit may be used.

In the present description, an "expression vector" is a vector including, in order from the upstream side, DNA having a promoter sequence, DNA having a sequence for incorporating foreign DNA, and DNA having a terminator sequence.

The aforementioned expression vector may be an expression vector for introduction into a prokaryotic cell such as *E. coli*, or an expression vector for introduction into a eukaryotic cell such as a yeast, a filamentous fungus, an insect cultured cell, a mammalian cultured cell, or a plant cell. Any arbitrary widely used expression vector can be selected and used in accordance with the respective host.

The expression vector according to the present invention is preferably an expression vector into which not only the aforementioned polynucleotide according to the present invention, but also a drug resistance gene or the like, has been incorporated. This facilitates the screening of cells transformed by the expression vector and non-transformed cells.

Examples of the drug resistance gene include a kanamycin resistance gene, a hygromycin resistance gene and a bialaphos resistance gene.

[Transformant]

The transformant according to the present invention is a transformant into which the expression vector according to the present invention has been introduced. In this transformant, the thermostable cellobiohydrolase according to the present invention can be expressed. Conventionally known cellobiohydrolases tend to have a narrow range of expression hosts, meaning heterologous expression is often difficult. However, the thermostable cellobiohydrolase according to the present invention can be expressed in a wide range of expression hosts, including *E. coli*, yeasts, filamentous fungi and higher plant chloroplasts. Accordingly, the host into which the expression vector is introduced may be a prokaryotic cell such as *E. coli*, or a eukaryotic cell such as a yeast, a filamentous fungus, an insect cultured cell, a mammalian cultured cell, or a plant cell. In other words, examples of the transformant according to the present invention include *E. coli*, a yeast, a filamentous fungus, an insect cultured cell, a mammalian cultured cell or a plant cell into which the expression vector according to the present invention has been introduced. By culturing a transformant of *E. coli*, the thermostable cellobiohydrolase according to the present invention can be generated more easily and in large amounts. On the other hand, because proteins are glycosylated in eukaryotic cells, by using a transformant of a eukaryotic cell, a thermostable cellobiohydrolase can be generated which exhibits superior thermal stability to that achieved by using a transformant of a prokaryotic cell.

There are no particular limitations on the method used for producing the transformant using the expression vector, and the types of methods typically used in the production of transformants can be employed. Examples of methods that can be used include an *Agrobacterium* method, a particle gun method, an electroporation method, and a PEG (polyethylene glycol) method. Of these, if the host is a plant cell, a particle gun method or an *Agrobacterium* method is preferred.

When a prokaryotic cell, a yeast, a filamentous fungus, an insect cultured cell, or a mammalian cultured cell or the like is used as the host, the obtained transformant can generally be cultured by a conventional method in a similar manner to that of the non-transformed host.

[Method for Producing Thermostable Cellobiohydrolase]

The method for producing a thermostable cellobiohydrolase according to the present invention is a method for generating a thermostable cellobiohydrolase in the aforementioned transformant according to the present invention. By culturing a transformant that has been produced using an expression vector into which the aforementioned polynucleotide according to the present invention has been incorporated downstream from a promoter having no ability to regulate the timing or the like of the expression, the thermostable cellobiohydrolase according to the present invention can be expressed constitutively within the transformant. On the other hand, in the case of a transformant produced using a so-called expression inducible promoter to induce the expression by means of a specific compound or temperature condition or the like, the thermostable cellobiohydrolase according to the present invention can be expressed in the transformant by culturing the transformant, and then conducting an induction treatment suitable for the respective expression-inducing condition.

The thermostable cellobiohydrolase generated by the transformant may be used in a state where it is retained inside the transformant, or may be extracted from the transformant and purified.

The method used for extracting and purifying the thermostable cellobiohydrolase from the transformant is not particularly limited, as long as the method does not impair the activity of the thermostable cellobiohydrolase, and extraction can be carried out by methods commonly used for extracting polypeptides from cells or biological tissue. Examples of the method include a method in which the transformant is immersed in an appropriate extraction buffer to extract the thermostable cellobiohydrolase, and the resulting liquid extract and the solid residue are then separated. The extraction buffer preferably contains a solubilizing agent such as a surfactant. If the transformant is a plant, then the transformant may be shredded or crushed prior to immersion in the extraction buffer. Further, in terms of the method used for separating the liquid extract and the solid residue, known solid-liquid separation treatments such as a filtration method, pressurized filtration method or centrifugation treatment may be used, or the extraction buffer containing the immersed transformant may be squeezed. The thermostable cellobiohydrolase in the liquid extract can be purified by known purification methods such as a salting-out method, ultrafiltration method, or chromatography method.

If the thermostable cellobiohydrolase according to the present invention is expressed in the transformant in a state having a secretory signal peptide, then a solution containing the thermostable cellobiohydrolase can be readily obtained by culturing the transformant and then collecting the culture liquid supernatant obtained by removal of the transformant from the obtained culture. Further, if the thermostable cellobiohydrolase according to the present invention has a tag such as an His tag, then the thermostable cellobiohydrolase in the liquid extract or in the culture supernatant can be easily purified by an affinity chromatography method using the tag.

In other words, the method for producing a thermostable cellobiohydrolase according to the present invention includes generating the thermostable cellobiohydrolase within the transformant according to the present invention, and also includes, according to need, extracting the thermostable cellobiohydrolase from the transformant and purifying the thermostable cellobiohydrolase.

[Glycoside Hydrolase Mixture]

The glycoside hydrolase mixture according to the present invention includes the aforementioned thermostable cellobiohydrolase according to the present invention or a thermostable cellobiohydrolase produced by the method for producing a thermostable cellobiohydrolase according to the present invention, and at least one other glycoside hydrolase. The thermostable cellobiohydrolase produced by the aforementioned method for producing a thermostable cellobiohydrolase according to the present invention may be in a state where it is incorporated inside the transformant, or may be extracted from the transformant and purified. By using the thermostable cellobiohydrolase according to the present invention as a mixture with one or more other glycoside hydrolases in a cellulose hydrolysis reaction, materials containing cellulose, such as materials composed of lignocellulose containing persistent cellulose, hemicellulose and lignin, can be degraded more efficiently.

There are no particular limitations on the other glycoside hydrolase besides the aforementioned thermostable cellobiohydrolase included in the glycoside hydrolase mixture, as long as it exhibits cellulose hydrolysis activity. Examples of the other glycoside hydrolase besides the aforementioned thermostable cellobiohydrolase included in the glycoside hydrolase mixture include hemicellulases such as xylanases and i-xylosidases, as well as cellobiohydrolases, β-glucosidases and endoglucanases. The glycoside hydrolase mixture according to the present invention is preferably a mixture containing at least one glycoside hydrolase selected from among hemicellulases and endoglucanases in addition to the aforementioned thermostable cellobiohydrolase, and is more preferably a mixture containing both a hemicellulase and an endoglucanase in addition to the aforementioned thermostable cellobiohydrolase.

Among the various possibilities, the glycoside hydrolase mixture according to the present invention is preferably a mixture containing at least one glycoside hydrolase selected from the group consisting of xylanases, β-xylosidases, cellobiohydrolases other than the aforementioned thermostable cellobiohydrolase and endoglucanases in addition to the aforementioned thermostable cellobiohydrolase, and is more preferably a mixture containing all of a xylanase, a β-xylosidase, a cellobiohydrolase other than the aforementioned thermostable cellobiohydrolase and an endoglucanase in addition to the aforementioned thermostable cellobiohydrolase.

It is particularly preferable that the glycoside hydrolase mixture contains at least both the aforementioned thermostable cellobiohydrolase and a cellobiohydrolase of the GH6 family.

The reason for this preference is that by using a combination of the aforementioned thermostable cellobiohydrolase and a cellobiohydrolase of the GH6 family, a level of cellobiohydrolase activity can be obtained that is superior to that observed when either of the cellobiohydrolases is used alone.

The other glycoside hydrolase included in the glycoside hydrolase mixture is preferably a thermostable glycoside hydrolase having glycoside hydrolase activity at least at 65° C., and is more preferably a thermostable glycoside hydrolase having glycoside hydrolase activity at 65 to 80° C. By ensuring that all of the enzymes contained in the glycoside hydrolase mixture are thermostable (for example, have an optimum temperature for the enzymatic activity or a thermal denaturation temperature for the enzyme protein of 65° C. or higher), the cellulose degradation reaction by the glycoside hydrolase mixture can be conducted efficiently under high-temperature conditions. In other words, if the glycoside hydrolase mixture contains only thermostable glycoside hydrolases, then by using the glycoside hydrolase mixture in a hydrolysis treatment of a material containing cellulose, such as a material composed of lignocellulose containing cellulose, it becomes possible to conduct a hydrolysis reaction of the material in a high-temperature environment in which the hydrolysis temperature is from 65 to 80° C. (namely, a high-temperature hydrolysis). With this high-temperature hydrolysis, the amount of enzymes used and the time required for the hydrolysis can be reduced markedly, and the hydrolysis costs can be cut dramatically.

[Method for Producing Cellulose Degradation Product]

The method for producing a cellulose degradation product according to the present invention is a method for obtaining a cellulose degradation product (for example, a degradation product containing monosaccharides such as glucose), the method including hydrolyzing oligosaccharides generated by the hydrolysis of cellulose with the thermostable cellobiohydrolase according to the present invention, thereby producing monosaccharides. More specifically, the method for producing a cellulose degradation product is a method of producing a degradation product of a material containing cellulose, such as a material containing cellulose degradation products, by bringing the material containing cellulose into contact with the thermostable cellobiohydrolase according to the present invention, the transformant according to the present invention, a thermostable cellobiohydrolase produced using the method for producing a thermostable cellobiohydrolase according to the present invention, or the glycoside hydrolase mixture according to the present invention.

There are no particular limitations on the material containing cellulose, provided the material contains cellulose. Specific examples of the material include cellulosic biomass such as weeds and agricultural waste materials, or used paper or the like. The material is preferably subjected to a physical treatment such as crushing or shredding, a chemical treatment with acid or alkali or the like, or a treatment such as immersion or dissolution in an appropriate buffer, prior to being brought into contact with the thermostable cellobiohydrolase according to the present invention.

In other words, the method for producing a cellulose degradation product according to the present invention may also include subjecting the aforementioned material containing cellulose to a physical treatment, to a chemical treatment, or to immersion or dissolution in a buffer, prior to being brought into contact with the thermostable cellobiohydrolase according to the present invention.

The reaction conditions for the cellulose hydrolysis reaction by the thermostable cellobiohydrolase according to the present invention may be any conditions under which the thermostable cellobiohydrolase exhibits cellobiohydrolase activity. For example, in the absence of divalent metal ions, the reaction is preferably conducted at a temperature of 55 to 65° C. and a pH of 5.5 to 7.0, and is more preferably conducted at a temperature of 60 to 65° C. and a pH of 5.5 to 7.0. Further, in the presence of divalent metal ions, the reaction is preferably conducted at a temperature of 55 to 75° C. and a pH of 5.5 to 7.0, and is more preferably conducted at a temperature of 65 to 75° C. and a pH of 5.5 to 7.0. The reaction time for the hydrolysis reaction may be adjusted appropriately with due consideration of the type, the method of pretreatment, and the amount and the like of the cellulose material supplied to the hydrolysis reaction. For example, the hydrolysis reaction may be performed for a reaction time of 10 minutes to 100 hours, but in the case of degradation of a material containing cellulosic biomass, the hydrolysis reaction is typically performed for a reaction time of 1 to 100 hours.

In the hydrolysis reaction of the material containing cellulose, it is also preferable to use at least one other type of glycoside hydrolase in addition to the thermostable cellobiohydrolase according to the present invention. This other glycoside hydrolase may be similar to the glycoside hydrolases mentioned above for inclusion in the aforementioned glycoside hydrolase mixture, and is preferably a thermostable glycoside hydrolase having glycoside hydrolase activity at least at 65° C., and preferably at least at temperatures of 65 to 80° C. Further, one aspect of the aforementioned method for producing a cellulose degradation product uses the thermostable cellobiohydrolase according to the present invention, the transformant according to the present invention, or a thermostable cellobiohydrolase produced by the method for producing a thermostable cellobiohydrolase according to the present invention, whereas another aspect of the method uses the aforementioned glycoside hydrolase mixture.

EXAMPLES

Next, the present invention is described in further detail based on a series of examples, but the present invention is in no way limited by the following examples.

[Example 1] Cloning of Novel Thermostable Cellobiohydrolase from Compost Culture Sample <1> DNA Extraction from Compost Culture Sample and Whole Genome Sequencing (WGS)

With the purpose of searching for genes of thermostable cellobiohydrolases (having an optimum temperature of 55° C. or higher), nucleotide sequencing was conducted of the genomic DNA of the microbial flora contained in compost culture samples.

The compost culture sample WN12-A3 was prepared in the following manner. First, the compost was collected. The temperature of the compost upon collection was within a range from 25 to 72° C. Next, about 0.5 g of the collected compost, two 1.5 cm square sheets of a thick paper (about 250 mg, gel-blotting paper GB005, manufactured by Whatman plc) as a carbon source, and one dialysis tube having dimensions of 1.2 cm×1.5 cm made of regenerated cellulose (Spectra/Por 7 RC dialysis tube, manufactured by Spectrum Laboratories, Inc.) were added to 20 mL of a modified AGS liquid medium detailed in Table 1, and a rotary shaking culture was performed at 65° C. and 120 rpm using a 125 mL conical flask fitted with baffles.

After culturing for one week, and following confirmation of the disappearance of the carbon source from inside the conical flask and the proliferation of bacteria, 0.5 mL of the culture liquid was subcultured in a fresh 20 mL sample of the modified AGS liquid medium, and a carbon source was then added and culturing was performed in the same manner as described above. After three repetitions of this subculturing process, the bacterial cells were collected by centrifugation (5.000 rpm, 10 minutes, 4° C.).

TABLE 1

| Modified AGS medium components | (/L) |
| --- | --- |
| L-arginine | 1 g |
| $K_2HPO_4$ | 1 g |
| NaCl | 1 g |
| $MgSO_4 \cdot 7H_2O$ | 0.5 g |
| $Fe_2(SO_4)_3 \cdot 6H_2O$ | 10 mg |
| $CuSO_4 \cdot 5H_2O$ | 1 mg |
| $ZnSO_4 \cdot 7H_2O$ | 1 mg |
| $MnSO_4 \cdot 4H_2O$ | 1 mg |

DNA was extracted from the collected bacterial cells using a DNA extraction kit (ISOIL for Beads Beating, manufactured by Nippon Gene Co., Ltd.). One μg of the extracted DNA was subjected to shotgun sequencing of the genomic DNA using a GS FLX+ 454 manufactured by Roche Diagnostics Ltd.

Genomic DNA sequencing of the compost culture sample WN12-A3 (hereafter sometimes referred to as the "WN12-A3 metagenome") yielded a whole genome sequence (WGS) data set having an average read length of 363 bp, a total read number of 3,257,291, and a total quantity of sequenced genomes of 1.187 Gbp.

<2> Assembly and Statistics of Compost Culture Sample Genomic Data

The output from the Roche 454 (sff file) was subjected to a second base calling using Pyrobayes (Quinlan et al., Nature Methods, 2008, vol. 5, pp. 179 to 181), and a FASTA format sequence file and a quality value file were obtained. Ends were cut from the obtained sequence reads to improve quality, and the reads were assembled using the 454 Life Sciences assembly software Newbler version 2.7. Assembly was performed under settings including "minimum acceptable overlap match (mi)=0.9" and "option:—large (for large or complex genomes, speeds up assembly but reduces accuracy)".

The total contig length of all contigs assembled to at least 100 bp totaled 32,352,781 bp, and this data set was used for cellulase gene analysis. Of the total read length of 3,257,291 reads, 2,830,164 reads were assembled into 20,621 contigs. The average length of these contigs was 1,481 bp, and the maximum contig length was 66,836 bp.

<3> Prediction of Open Reading Frames (ORFs) of Cellobiohydrolase

Sequences having EC numbers of 3.2.1.4 (cellulase), 3.2.1.21 (β-glucosidase), 3.2.1.37 (β-xylosidase), 3.2.1.91 (cellulose 1,4-β-cellobiosidase) and 3.2.1.8 (endo-1,4-β-xylanase) were downloaded (date of access: 2011/12/9) from the UniProt database, and a proteome local database of these glycoside hydrolase genes was constructed. The annotation software MetaGeneAnnotator (Noguchi et al., MetaGeneAnnotator: Detecting Species-Specific Patterns of Ribosomal Binding Site for Precise Gene Prediction in Anonymous Prokaryotic and Phage Genomes, DNA Res., 2008, 15, pp. 387 to 396) was used to predict gene regions (=open reading frames) from the contig sequences obtained in the above section <2>. In order to extract glycoside hydrolase genes from the predicted ORFs, reference was made to the aforementioned local database using BLASTP (blastall ver. 2.2.18). Furthermore, the option conditions for BLASTP were set such that: "Filter query sequence=false", "Expectation value (E)<$1e^{-20}$" (hereafter, default values were set such that: "Cost to open a gap=−1", "Cost to extended gap=−1", "X dropoff value for gapped alignment=0", "Threshold for extending hits=0", and "Word size=default"), and the hit sequences were collected as glycoside hydrolase genes.

<4> Glycoside Hydrolase (GH) Family Classification of Genes

Functional classification of the sequences collected in section <3> above, including various sequences containing glycoside hydrolases such as cellulases, endohemicellulases and debranching enzymes, was performed with reference to the protein functional domain sequence database Pfam HMMs (Pfam version 23.0 and HMMER v2.3; Finn et al., Nucleic Acids Research Database, 2010, Issue 38, pp. D211 to 222). Specifically, the glycoside hydrolase (GH) family of each sequence was determined on the basis of homology with the Pfam domain database by using the protein motif search program HMMER (Durbin et al., "The theory behind profile HMMs. Biological sequence analysis: probabilistic models of proteins and nucleic acids", 1998, Cambridge University Press; hmmpfam (Ver. 2.3.2), E-value cutoff<$1e^{-5}$; Database=Pfam_fs (models that can be used to find fragments of the represented domains in a sequence)).

Based on homology search results by BLASTP and reference to Pfam HMMs using the sequence data from the compost culture sample WN12-A3, ten ORFs (6 full-length ORFs and 4 partial length ORFs) were predicted as being cellobiohydrolase genes. The GH family classification results of these genes are shown in Table 2. As shown in Table 2, one cellobiohydrolase full-length ORF belonging to each of the GH family 16 and the GH family 18, and two full-length ORFs belonging to each of the GH family 26 and the GH family 53 were obtained from the genome data for the compost culture sample WN12-A3. Primers were designed for all of these ORFs, and the genes were cloned from the compost culture sample-derived DNA by PCR. As a result, the cellobiohydrolase gene WN12-A3-v6-4-10-11 was isolated from the open reading frame WN12-A3-v6-4 belonging to the GH family 48 and having a cellobiohydrolase sequence.

TABLE 2

|                    | GH6 | GH16 | GH18 | GH26 | GH48 | GH53 | Total |
|--------------------|-----|------|------|------|------|------|-------|
| Full-length ORFs   | 0   | 1    | 1    | 2    | 0    | 2    | 6     |
| Partial length ORFs| 1   | 0    | 0    | 1    | 2    | 0    | 4     |
| Total              | 1   | 1    | 1    | 3    | 2    | 2    | 10    |

<5> Open Reading Frame WN12-A3-v6-4

The open reading frame WN12-A3-v6-4 encoded a polypeptide (SEQ ID NO: 1) composed of 784 amino acid residues, and was a partial length sequence (SEQ ID NO: 2) in which the aforementioned polypeptide had an amino acid residue at position 1 that started from a methionine (M) but lacked a termination codon at the 3'-end. Based on the sequence homology of the motif, it was predicted that in the polypeptide encoded by the open reading frame WN12-A3-v6-4, the 40 amino acid residues from the methionine at position 1 through to the alanine (A) at position 40 represented a secretory signal (SignalP 4.1), and the 695 amino acid residues from the arginine (R) at position 47 through to the leucine (L) at position 741 encoded the catalytic domain of the glycoside hydrolase family 48. This ORF was a novel sequence that exhibited 77% amino acid sequence identity in the GH48 catalytic domain with the cellulose 1,4-β-cellobiosidase from the Firmicutes bacterium *Paenibacillus* subsp. FSL H7-689 (Genbank registration ID: ETT50502.1) (SEQ ID NO: 7). The sequence homology was calculated using the ClustalW algorithm.

Figure 1:
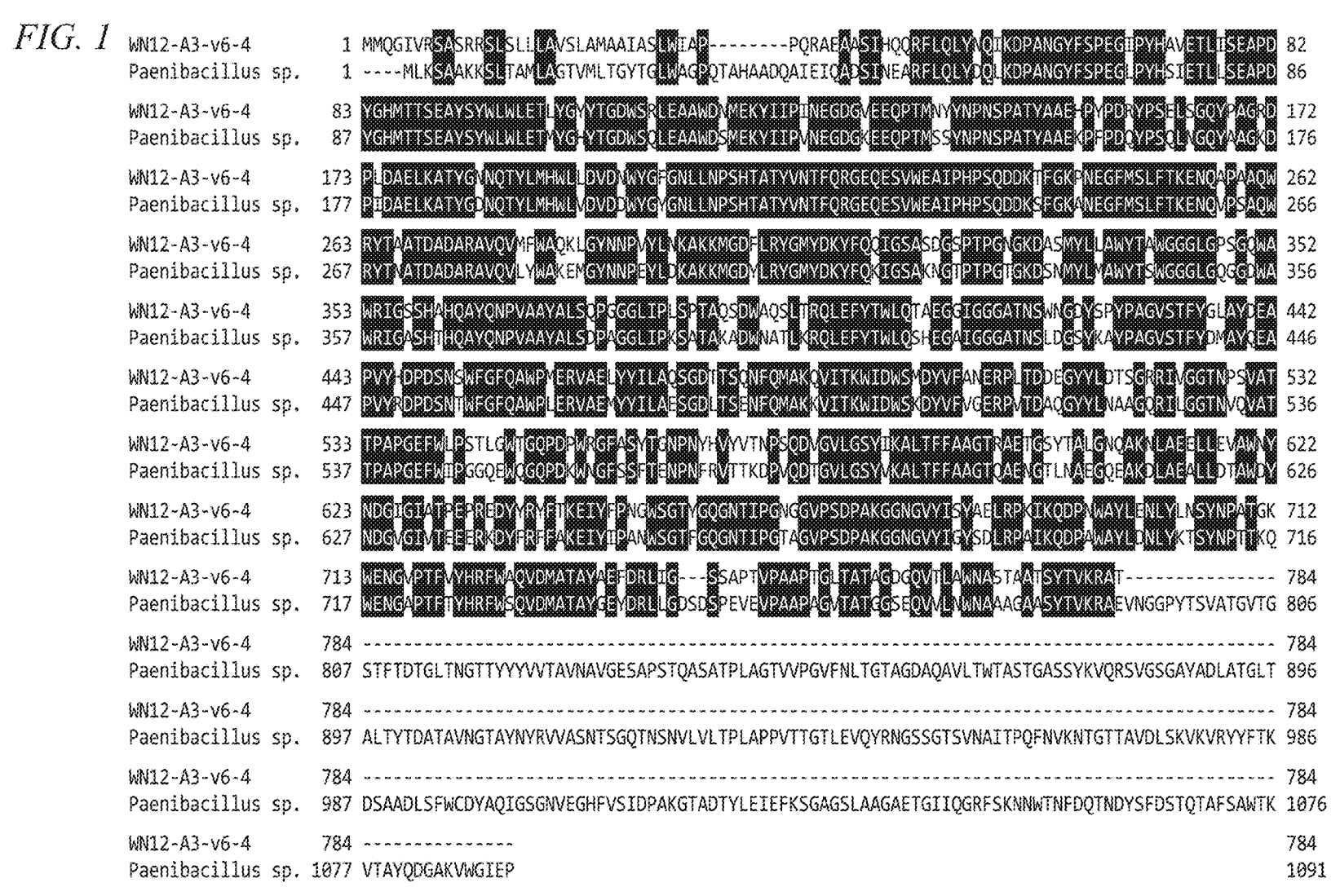

FIG. 1 shows the alignment of the amino acid sequence (SEQ ID NO: 1) of the polypeptide presumed to be encoded by the open reading frame WN12-A3-v6-4 and the amino acid sequence (SEQ ID NO: 7) of the cellulose 1,4-β-cellobiosidase from the Firmicutes bacterium *Paenibacillus* subsp. FSL H7-689. In FIG. 1, the amino acids shown in white on black are the amino acid residues identical to both amino acid sequences, and "-" indicates a gap in a sequence.

<6> Cellobiohydrolase Gene WN12-A3-v6-4-10-11

PCR cloning was used to isolate the cellobiohydrolase gene WN12-A3-v6-4-10-11 from the open reading frame WN12-A3-v6-4 (SEQ ID NO: 1) predicted as a cellobiohydrolase gene open reading frame. The WN12-A3-v6-4-10-11 gene included a nucleotide sequence composed of 2,352 bp that was identical with the open reading frame WN12-A3-v6-4.

<7> Expression and Purification of Cellobiohydrolase Protein

Using a forward primer including a nucleotide sequence represented by SEQ ID NO: 5 (5'-GTGATATGATCA-GGGAATCGTTCGA-3': wherein three nucleotides (GTG) were added to the 5'-end of the nucleotide sequence represented by SEQ ID NO: 3, and the 5'-end was phosphorylated), and a reverse primer including a nucleotide sequence of SEQ ID NO: 6 (5'-ATGCAAAGCTTTTAGGTG-GCGCGCTTCACCGTG-3': wherein a termination codon and a recognition sequence for the restriction enzyme Hind III were added to the 5'-end of the nucleotide sequence represented by SEQ ID NO: 4, the Hind III being a sequence used for vector insertion), a PCR product that had been amplified by KOD-Plus-Neo (manufactured by Toyobo Co., Ltd.) was inserted into a pLEAD5 vector (manufactured by Nippon Gene Co., Ltd.) and transformed into an *E. coli* JM109 strain using the WN12-A3-v6-4-10-11 gene that had been isolated by PCR cloning as a template. The nucleotide sequence represented by SEQ ID NO: 3 is homologous (identical) with the partial sequence composed of the nucleotides from positions 1 to 21 of the nucleotide sequence represented by SEQ ID NO: 2. Further, the nucleotide sequence represented by SEQ ID NO: 4 is complementary with the partial sequence composed of the nucleotides from positions 2,334 to 2,352 of the nucleotide sequence represented by SEQ ID NO: 2. Positive clones were selected by colony PCR and cultured in an LB liquid medium containing 50 mg/L of ampicillin at a temperature of 37° C. and 200 rpm for 17 to 20 hours, and then plasmids were prepared using a miniprep kit (Wizard plus SV Minipreps DNA Purification System, manufactured by Promega Corporation).

Sequence confirmation of the prepared plasmids was performed using a sequencer (3730 DNA Analyzer, manufactured by Life Technologies Corporation).

The transformed *E. coli* clone having the WN12-A3-v6-4-10-11/pLEAD5 plasmid for which the sequence had been confirmed was inoculated into a Turbo Broth medium (manufactured by Athena Environmental Sciences, Inc.) containing 50 mg/L of ampicillin, and was cultured for about 20 hours to express the target protein. Following culturing, the *E. coli* was collected by centrifugation, and an amount of 50 mM Tris-HCl buffer (pH 8.0) equivalent to ¹/₁₀ of the volume of the culture liquid was added and suspended. Subsequently, a process consisting of 5 minutes disrupting and then 5 minutes of rest was repeated 7 or 8 times using an ultrasonic disrupter Astrason 3000 (manufactured by MISONIX Inc.), thus obtaining a crude extract of the gene recombinant *E. coli* containing the target protein. This gene recombinant *E. coli* crude extract was filtered through a filter (pore size $\phi=0.45$ μm, manufactured by EMD Millipore Corporation), and the resulting filtrate was used as a gene recombinant *E. coli* homogeneous supernatant.

The gene recombinant *E. coli* homogeneous supernatant was loaded onto an ion exchange column HiTrap Q HP (manufactured by GE Healthcare, Inc.) equilibrated with a 50 mM Tris-HCl buffer (pH 8.0), and a medium-high pressure liquid chromatography system AKTA design (manufactured by GE Healthcare, Inc.) was used to fractionate proteins with a concentration gradient of 0 to 50% in a 50 mM Tris-HCl buffer (pH 8.0) containing 1 M of NaCl. The fractions exhibiting cellobiohydrolase activity were pooled, and a centrifugal ultrafiltration membrane VIVAS-PIN 20 (manufactured by Sartorius stedim Biotech SA) was used to exchange the buffer to a 50 mM Tris-HCl buffer (pH 8.0) containing 750 mM of ammonium sulfate. The fractions with cellobiohydrolase activity following the buffer exchange were loaded onto a hydrophobic interaction separation column HiTrap Phenyl HP (manufactured by GE Healthcare, Inc.) equilibrated with the same buffer solution, and the proteins were fractionated with a concentration gradient of 0 to 100% in a 50 mM Tris-HCl buffer (pH 8.0). The fractions exhibiting cellobiohydrolase activity were pooled and then concentrated using the VIVASPIN 20 until the liquid volume reached about 8 mL. The concentrated sample was loaded onto a gel filtration column Hiload 26/60 superdex 200 pg (manufactured by GE Healthcare, Inc.) equilibrated with a 50 mM Tris-HCl buffer (pH 8.0) containing 150 mM of NaCl, and was fractionated by passing a volume of the same buffer equivalent to 1 to 1.5 times the column volume through the column at a flow rate of 2 to 3 mL/min. The fractions exhibiting cellobiohydrolase activity were pooled, a buffer exchange to a 50 mM Tris-HCl buffer (pH 8.0) and subsequent concentration were performed using the VIVASPIN 20, and the proteins were fractionated in the same manner as that described above using the HiTrap Q HP. The fractions exhibiting cellobiohydrolase activity were pooled, and a buffer exchange to a 50 mM Tris-HCl buffer (pH 8.0) and subsequent concentration were performed, yielding a purified enzyme with a final concentration of about 1 mg/mL.

The gene recombinant E. coli homogenous supernatant and the purified enzyme (purified cellobiohydrolase protein) were checked by SDS-PAGE analysis (SDS-polyacrylamide gel electrophoresis). The SDS electrophoresis of the gene recombinant E. coli homogenous supernatant and the purified enzyme was performed using a Mini-PROTEAN TGX Stain-Free gel (manufactured by Bio-Rad Laboratories, Inc.). The supernatant and the purified enzyme were each mixed with Tris-SDS βME treatment solution (manufactured by Cosmo Bio Co. Ltd.) at 1:1, and following treatment of the thus obtained electrophoresis samples at 100° C. for 10 minutes, a 10 μL sample of the gene recombinant E. coli homogenous supernatant and a 0.5 μg sample of the purified enzyme respectively were subjected to electrophoresis. Following completion of the electrophoresis, the protein bands were visualized and detected by CBB staining.

FIG. 2 shows the SDS-PAGE analysis results of the gene recombinant E. coli homogenous supernatant prepared from the transformed E. coli into which the WN12-A3-v6-4-10-11 gene had been introduced, and the purified enzyme produced from the gene recombinant E. coli homogenous supernatant. The figure shows an electrophoretic pattern in which lane 1 represents a protein mass marker, lane 2 represents the gene recombinant E. coli homogenous supernatant, and lane 3 represents the purified enzyme.

The results revealed a strong band in the gene recombinant E. coli homogenous supernatant (lane 2) near the mass of 86.9 kDa expected from the amino acid sequence (SEQ ID NO: 1), and a single band corresponding with this band (indicated by an arrow in the figure) was observed in the purified enzyme (lane 3).

<8> Cellobiohydrolase Activity Against PSA Substrate

The cellobiohydrolase activity of the enzyme protein (WN12-A3-v6-4-10-1) encoded by the WN12-A3-v6-4-10-1 gene against a substrate of PSA was investigated. In the measurements, a solution prepared by diluting the purified enzyme obtained in section <7> above with a 0.05 M Tris-HCl buffer (pH 8.0) to obtain a concentration of 1 mg/mL was used.

The PSA used as the substrate was prepared by first dissolving an Avicel powder (microcrystalline cellulose powder, manufactured by Merck & Co., Inc.) in a phosphoric acid solution, subsequently adding purified water to cause precipitation, and then washing until a pH of 5 or greater was obtained. The PSA used in the experiments described below was all prepared by the above method.

A sample tube with a volume of 1.5 mL was used as the reaction vessel, and the reaction solution was composed of 10 μL of the diluted purified enzyme, 40 μL of purified water, 50 μL of a 200 mM acetate buffer (pH 6), and 100 μL of a 1% by mass PSA solution. In all measurements, a mixed solution prepared by replacing the purified enzyme solution with a 50 mM Tris-HCl buffer (pH 8.0) and then reacting the solution under the same conditions was used as a control. Further, the substrate solution and the mixed solution containing the purified enzyme solution, the purified water and the buffer were held separately at the reaction temperature for five minutes (pre-incubation) before being mixed to initiate the reaction. During reaction, all of the mixed solutions were adjusted to the prescribed temperature using a Thermomixer (manufactured by Eppendorf AG). Following completion of the 20-minute reaction, 3,5-dinitrosalicylic acid reagent (DNS solution) was added to each reaction solution in a volume equal to that of the solution, and the resulting mixture was heated at 100° C. for 5 minutes, cooled on ice for 5 minutes, and then centrifuged at 17,500 g for 5 minutes at room temperature to obtain a supernatant. The amount of reducing sugars within the supernatant was determined by measuring the absorbance at 540 nm using a spectrophotometer, calculating the amount of reducing sugars using a calibration curve prepared with glucose, and then calculating the amount of reducing sugars produced by the enzymatic hydrolysis based on the difference from the control. The enzymatic activity for producing 1 μmol of reducing sugars per minute was defined as 1 U, and the value obtained by dividing this activity by the amount of protein was defined as the specific activity (U/mg). Each measurement was performed for three independent experiments, and a mean value and a standard error were determined.

<9> Substrate Specificity of WN12-A3-v6-4-10-11

The hydrolysis activity of the enzyme protein WN12-A3-v6-4-10-11 against various cellulose substrates and hemicellulose substrates was investigated. In the measurements, a solution prepared by diluting the purified enzyme obtained in section <7> above with a 0.05 M Tris-HCl buffer (pH 8.0) to obtain a concentration of 1 mg/mL was used. For the substrates, PSA, Avicel powder, CMC (manufactured by Sigma-Aldrich Co. LLC.), xylan (derived from beech wood, manufactured by Sigma-Aldrich Co. LLC.), lichenan (manufactured by MP Biomedicals. LLC), laminarin (derived from Laminaria digitata, manufactured by Sigma-Aldrich Co. LLC.), PNPC (manufactured by Sigma-Aldrich Co. LLC.) and PNPG (manufactured by Sigma-Aldrich Co. LLC.) were used.

Specifically, when PSA, Avicel powder, CMC, xylan, lichenan or laminarin was used as the substrate, with the exception of using a 1% by mass aqueous solution as the substrate solution and performing the reaction at 65° C., reaction was performed in the same manner as that described above in section <8>, the amount of reducing sugars produced by the enzymatic hydrolysis was determined, and the specific activity (U/mg) was calculated. For the xylan measurement, a calibration curve prepared using xylose was used.

When PNPC or PNPG was used as the substrate, with the exception of using a 10 mM aqueous solution as the substrate solution and performing the reaction at 65° C., reaction was first performed in the same manner as that described above in section <8>, and following the 20-minute reaction, an equal volume of a 200 mM aqueous solution of sodium carbonate was added, and the resulting mixture was then centrifuged for 5 minutes to obtain a supernatant. The amount of p-nitrophenol in the supernatant was determined by measuring the absorbance at 420 nm using a spectrophotometer, calculating the amount of p-nitrophenol in the supernatant using a calibration curve prepared with p-nitrophenol, and then determining the amount of p-nitrophenol produced by the enzymatic hydrolysis on the basis of the difference from the control. The enzymatic activity for producing 1 μmol of p-nitrophenol per minute was defined as 1 U, and the value obtained by dividing this activity by the amount of protein was defined as the specific activity (U/mg).

Figure 3:
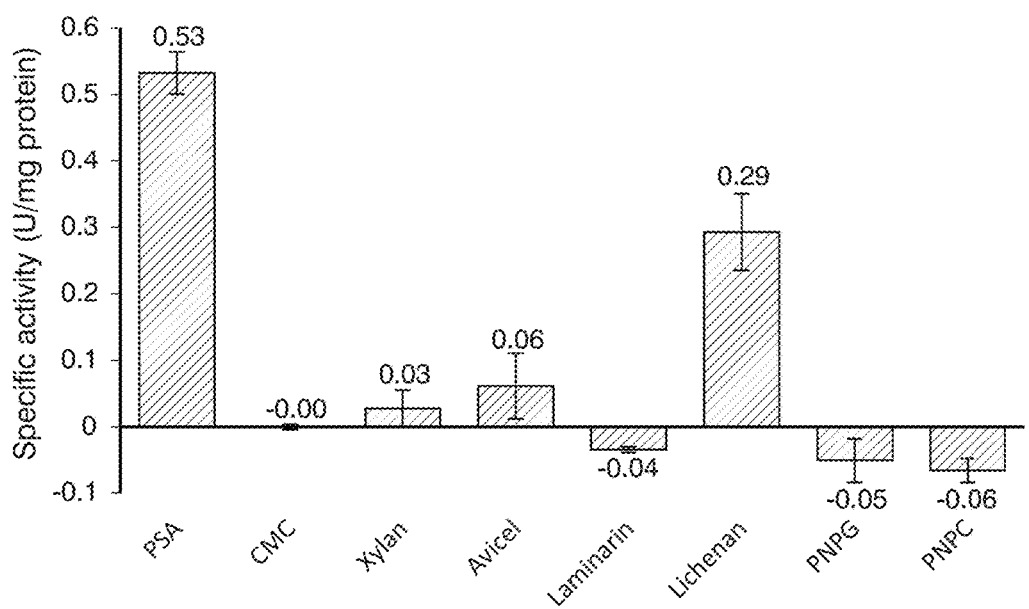
FIG. 3 is a diagram showing the results of measuring the hydrolysis activity against various substrates of the WN12-A3-v6-4-10-11 protein obtained by expressing the WN12-A3-v6-4-10-11 gene in *E. coli* in Example 1.

The measurement results are shown in FIG. 3. The results revealed that WN12-A3-v6-4-10-11 exhibited hydrolysis activity against PSA, and also exhibited weak hydrolysis activity against Avicel and lichenan, but exhibited almost no hydrolysis activity against CMC, laminarin, xylan, PNPG and PNPC.

<10> Temperature and pH Dependencies of Cellobiohydrolase Activity of WN12-A3-v6-4-10-11

The temperature dependency of the PSA hydrolysis activity of WN12-A3-v6-4-10-11 was investigated.

Specifically, with the exception of setting the reaction temperature to 50, 55, 60, 65, 70, 75, 80 or 85° C., reaction was performed in the same manner as that described above in section <8>, and for each temperature, the amount of reducing sugars produced by the enzymatic hydrolysis was determined and the PSA hydrolysis activity (U/mg) was calculated.

Further, measurements were also performed using reaction solutions in which a 10 mM aqueous solution of $CaCl_2$ was added instead of the 40 µL of purified water, and for each temperature, the amount of reducing sugars produced by the enzymatic hydrolysis was determined and the PSA hydrolysis activity (U/mg) was calculated.

Figure 4:
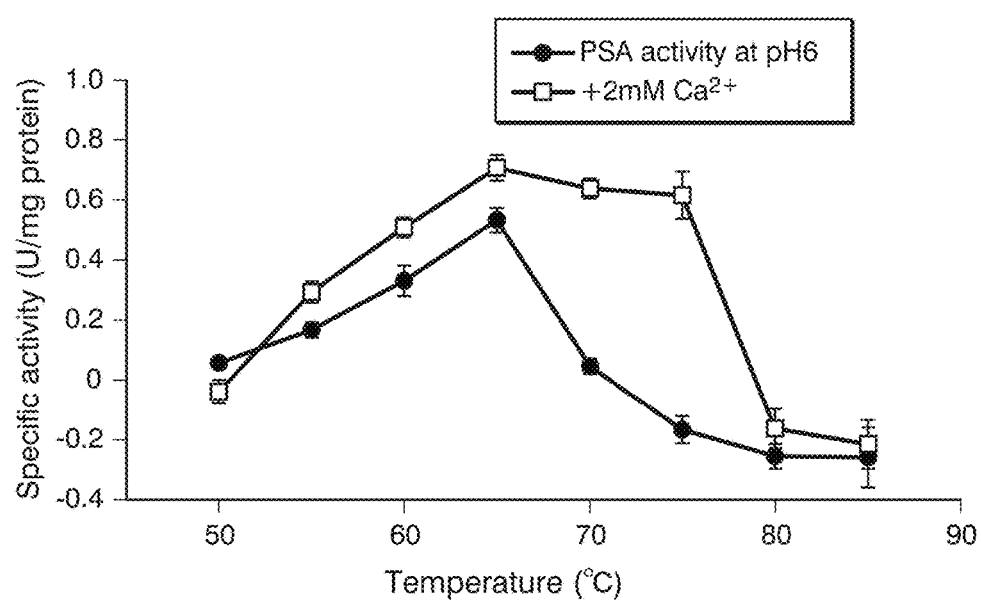
FIG. 4 is a diagram showing the results of measuring the PSA hydrolysis activity (pH 6) at various temperatures, either in the presence of calcium ions or in the absence of calcium ions, of the WN12-A3-v6-4-10-11 protein obtained by expressing the WN12-A3-v6-4-10-11 gene in *E. coli* in Example 1.

The results are shown in FIG. 4. In the absence of calcium ions (labeled as "PSA activity at pH 6" in the figure), WN12-A3-v6-4-10-11 exhibited PSA hydrolysis activity in a temperature range from 50 to 70° C. Further, in the presence of calcium ions (labeled as "+2 mM $Ca^{2+}$" in the figure), WN12-A3-v6-4-10-11 exhibited PSA hydrolysis activity in a temperature range from 55 to 75° C. The optimum temperature ($T_{opt}$) at which the highest activity was observed was 65° C. in the absence of calcium ions, and the activity decreased rapidly above that temperature. In contrast, in the presence of calcium ions, although the optimum temperature was 65° C., no significant reduction in activity was observed until 75° C. The activity at 75° C. was maintained at 87% of the activity at the optimum temperature.

The pH dependency of the PSA hydrolysis activity of WN12-A3-v6-4-10-11 was also investigated.

Specifically, with the exception of performing the reaction at 60° C. using 50 µL of a 200 mM McIlvaine buffer (pH 4 to 8), reaction was performed in the same manner as that described above in section <8>, and for each pH value, the amount of reducing sugars produced by the enzymatic hydrolysis was determined and the PSA hydrolysis activity (U/mg) was calculated.

Figure 5:
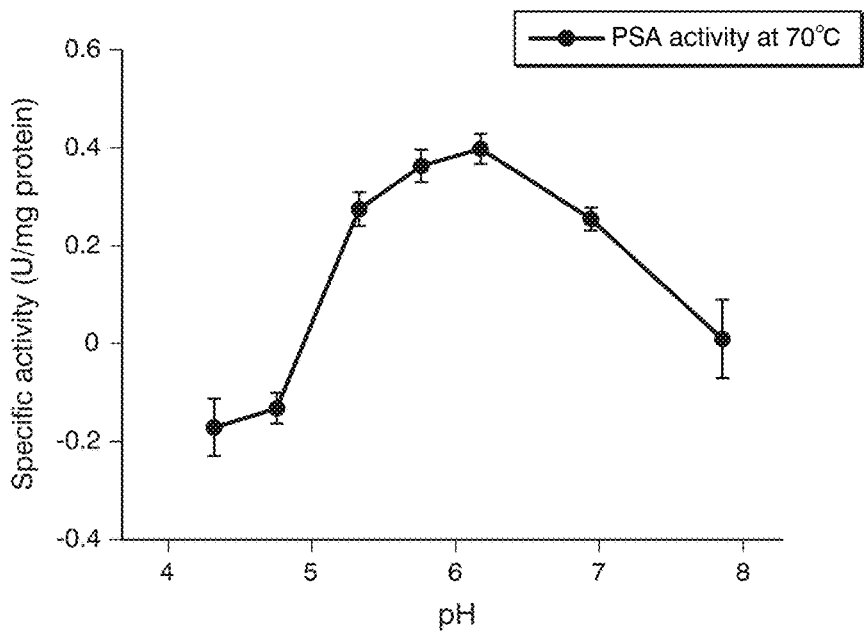
FIG. 5 is a diagram showing the results of measuring the PSA hydrolysis activity (60° C.) at various pH values of the WN12-A3-v6-4-10-11 protein obtained by expressing the WN12-A3-v6-4-10-11 gene in *E. coli* in Example 1.

The results are shown in FIG. 5. For the pH values, the actual measurement value obtained for the mixed solution containing the substrate, the buffer and the enzyme was plotted. WN12-A3-v6-4-10-11 exhibited PSA hydrolysis activity in a pH range from pH 5 to 7. The optimum pH was 6.18 (actual measurement value for the mixed solution containing the substrate, the buffer and the enzyme).

<11> Cellobiohydrolase Activity of WN12-A3-v6-4-10-11 when Mixed with GH6 Cellobiohydrolase The cellulose hydrolysis activity of a mixture of WN12-A3-v6-4-10-11 and a GH6 cellobiohydrolase was investigated. Using AR19G-166-RA (SEQ ID NO: 8) as the GH6 cellobiohydrolase, the mixing ratio (mass ratio) with the WN12-A3-v6-4-10-11 was changed within a range from 10:0 to 0:10 without altering the total amount of enzyme, and the PSA hydrolysis activity and the Avicel hydrolysis activity were measured. Specifically, reaction solutions composed of 10 µL of a mixed solution of the purified enzymes, 40 µL of a 10 mM $CaCl_2$ solution, 50 µL of a 200 mM acetate buffer (pH 6), and 100 µL of a 1% by mass aqueous solution of PSA or Avicel were reacted, either at 70° C. for 20 minutes in the case of the PSA substrate, or at 70° C. for 2 hours in the case of the Avicel substrate. Following reaction, the amount of reducing sugars produced by the enzymatic hydrolysis was determined, and the specific activity (U/mg) was calculated in the same manner as that described above in section <8>. The enzymatic activity was recorded as a relative activity value (%), relative to a value of 100% for the activity when the mixing ratio between the AR19G-166-RA and WN12-A3-v6-4-10-11 was 10:0 (namely, the case where the amount of WN12-A3-v6-4-10-11 was 0%).

Figure 6:
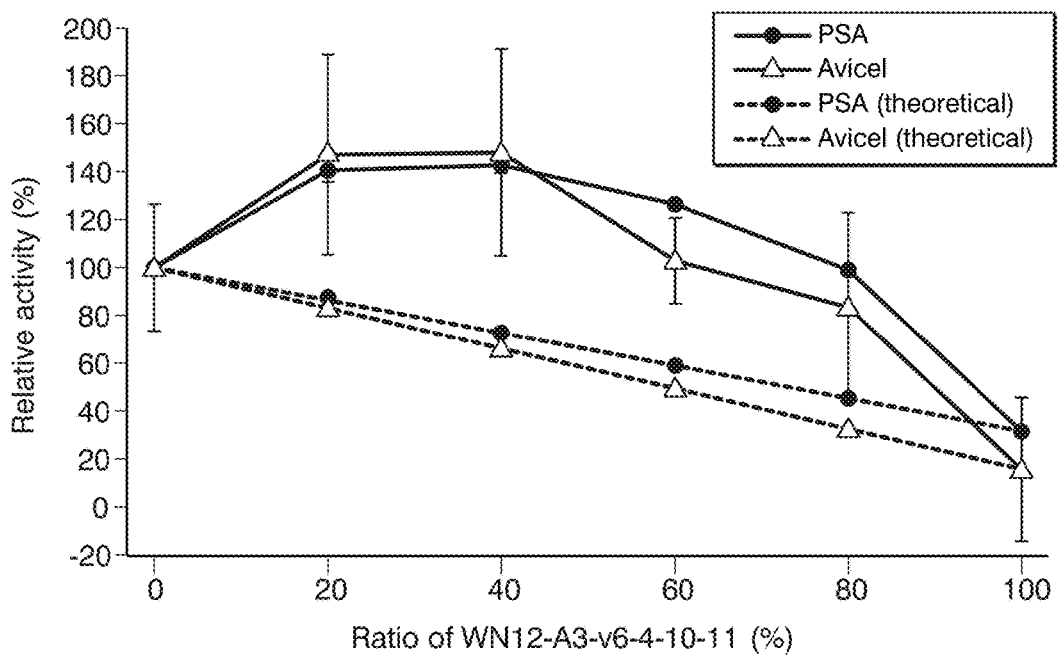
FIG. 6 is a diagram showing the results of measuring the PSA hydrolysis activity and the Avicel hydrolysis activity (pH 6, 70° C.) of various enzyme compositions obtained by mixing, in various proportions, the WN12-A3-v6-4-10-11 protein obtained by expressing the WN12-A3-v6-4-10-11 gene in *E. coli* and a GH6 cellobiohydrolase AR19G-166-RA obtained by expression in *E. coli* in Example 1.

The results are shown in FIG. 6. In FIG. 6, the horizontal axis represents the proportion (amount (%)) of WN12-A3-v6-4-10-11 relative to the total amount of enzyme. In the figure, the theoretical values expected for the combination of AR19G-166-RA and WN12-A3-v6-4-10-11 assuming no synergistic effect are shown as dotted lines. The PSA hydrolysis activity and the Avicel hydrolysis activity exceeded the corresponding theoretical value at all of the mixing ratios, confirming a synergistic effect between AR19G-166-RA and WN12-A3-v6-4-10-11. Hydrolysis activity that was superior to that obtained when AR19G-166-RA was used alone was confirmed for those cases where the proportion of WN12-A3-v6-4-10-11 was within a range from 20% to 60% in the case of the PSA hydrolysis activity, and for those cases where the proportion of WN12-A3-v6-4-10-11 was within a range from 20% to 40% in the case of the Avicel hydrolysis activity. Maximum values were observed for both the PSA hydrolysis activity and the Avicel hydrolysis activity when the proportion of the WN12-A3-v6-4-10-11 was from 20% to 40%, and the respective increases in the hydrolysis activity values were about 40% and about 50%. In this manner, a synergistic effect between the WN12-A3-v6-4-10-11 and the GH6 family cellobiohydrolase yields a maximum increase in the cellobiohydrolase activity of about 50% compared with the activity values observed when using either enzyme alone, which is ideal for improving the efficiency of cellulose hydrolysis processes.

<12> Thermal Stability Measurement of Cellobiohydrolase by Differential Scanning Fluorimetry Differential scanning fluorimetry (DSF) is one of the methods of measuring the thermal denaturation of proteins using a fluorescent dye and a real-time PCR machine, and can be applied to all manner of proteins. The fluorescent dyes used in DSF such as SYPRO Orange emit fluorescence under nonpolar conditions when bound to a hydrophobic region, while the emission is suppressed under the polar conditions produced upon dissolution in water. Usually, the protein structure unfolds at the thermal denaturation temperature, and the internal hydrophobic regions of the protein are exposed at the protein surface. When SYPRO Orange binds to such an exposed hydrophobic region, excitation light having a wavelength of 470 to 480 nm causes emission of a strong fluorescence having a peak near a wavelength of 595 nm. By increasing the temperature of the protein solution at regular intervals in a stepwise manner and measuring the fluorescence intensity, the thermal denaturation temperature (=change point of the fluorescence intensity) can be calculated.

Measurements were performed using a purified enzyme solution prepared by dissolving the purified enzyme WN12-A3-v6-4-10-11 obtained in section <7> above in water at a concentration of 1 mg/mL.

Specifically, 2 µL of 100-fold diluted SYPRO Orange (manufactured by Life Technologies Inc.), 1 µL of the purified enzyme solution with a concentration of 1 mg/mL, 5 µL of a 200 mM acetate buffer (pH 6) and 12 µL of either purified water or a solution prepared by mixing purified water and a 10 mM $CaCl_2$ solution in a ratio of 2:1 were added to each well of a 96-well PCR plate (Multiplate 96 Well PCR Plate MLL-9651, manufactured by Bio-Rad Laboratories, Inc.) so that the volume in each well was 20 µL. The PCR plate was sealed with Optical Flat 8-Cap Strips (manufactured by Bio-Rad Laboratories, Inc.), the temperature of each well was increased in steps of 0.2° C. from 30° C. up to 100° C. using a real-time PCR machine (CFX96 Touch Real-Time PCR System, manufactured by Bio-Rad Laboratories, Inc.), and following a pause of 10 seconds after each target temperature was achieved, the fluorescence intensity of each well was measured simultaneously. The SYPRO Orange was excited by a light emitting diode (LED) having a wavelength range of 450 to 490 nm, the emitted light from the SYPRO Orange was passed through a band pass filter having a range of 560 to 580 nm, a CCD camera was used to measure the fluorescence intensity, and the change in fluorescence intensity was plotted as a function of temperature. The thermal denaturation temperature (melting temperature; Tm value) was defined as the local minimum value of the first derivative of the fluorescence intensity curve plotted as a function of temperature ("−d(Fluorescence)/dt" shown on the Y axis of FIG. 7(B)). Data analysis was conducted using the analysis software CFX Manager (manufactured by Bio-Rad Laboratories, Inc.) supplied with the real-time PCR machine. Each measurement was performed for three independent experiments, and a mean value and a standard error were determined.

Figure 7:
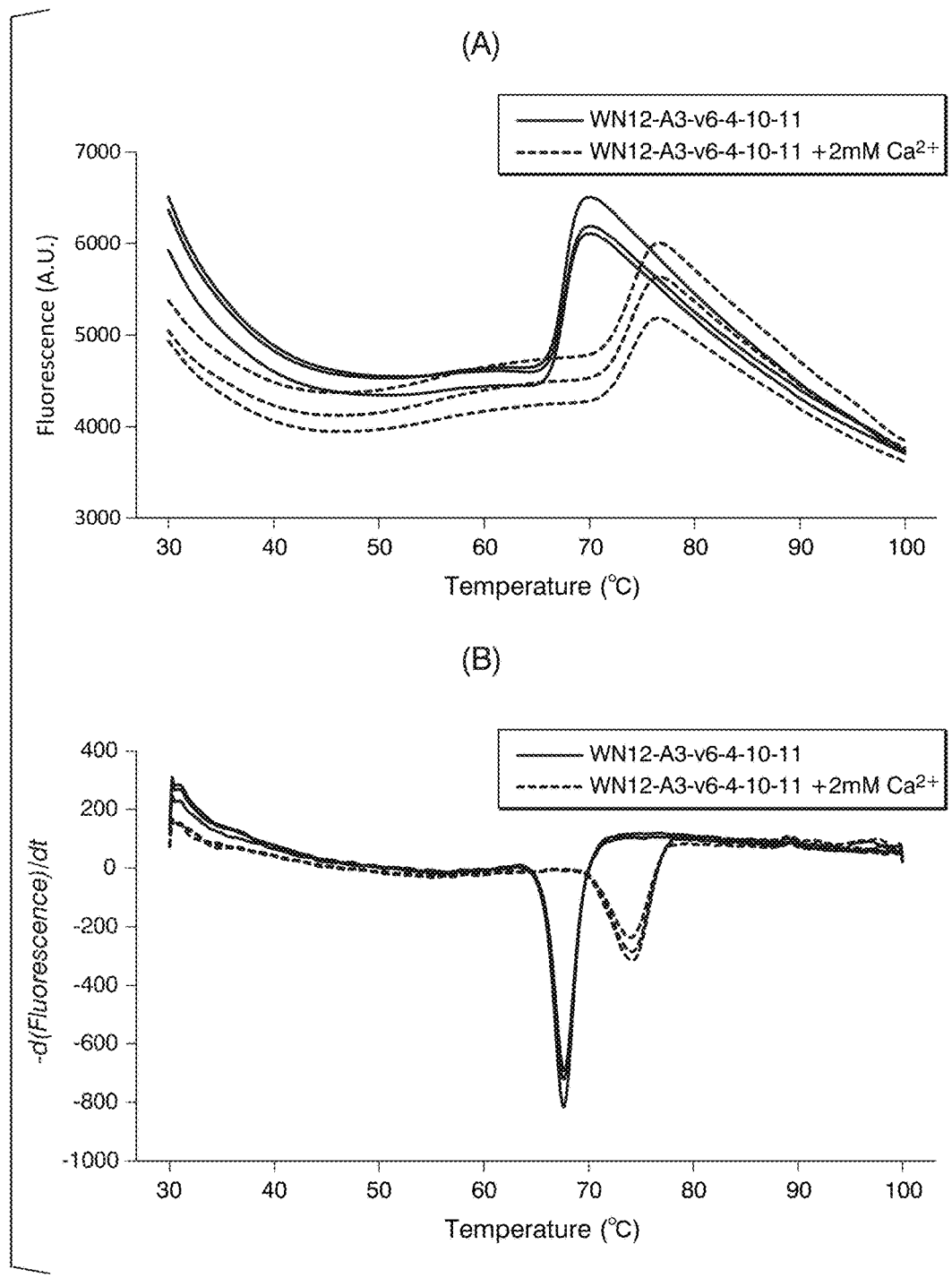
FIG. 7 consists of a diagram (A) and a diagram (B). The diagram (A) shows actual measurement data of the change in the fluorescence intensity of SYPRO Orange that is generated in association with the thermal denaturation exhibited by the WN12-A3-v6-4-10-11 protein obtained by expressing the WN12-A3-v6-4-10-11 gene in *E. coli* in Example 1. The diagram (B) shows a first derivative "–d (Fluorescence)/dt" of the fluorescence intensity change curve of the diagram (A).

FIG. 7 shows the change in the fluorescence intensity of SYPRO Orange measured by the DSF method and caused in association with the thermal denaturation exhibited by the WN12-A3-v6-4-10-11 enzyme protein. FIG. 7(A) shows the actual measurement data, and FIG. 7(B) shows the first derivative "−d(Fluorescence)/dt" of the fluorescence intensity change curve of FIG. 7(A).

The first derivative of the fluorescence intensity of WN12-A3-v6-4-10-11 had a local minimum point near 68° C., indicating that thermal denaturation occurs at that temperature. Further, under the conditions including added $CaCl_2$, the local minimum point occurred near 74° C. The average values for the thermal denaturation temperature were 67.6±0° C. (no $CaCl_2$ addition) and 74.1±0.1° C. ($CaCl_2$ addition), confirming that the inclusion of calcium ions increased the thermal denaturation temperature by 6.5° C.

The invention claimed is:

1. A polypeptide having cellobiohydrolase activity, wherein the polypeptide comprises the amino acid sequence of SEQ ID NO: 1 and a heterologous amino acid sequence selected from the group consisting of a cellulose-binding module, a linker, a signal peptide and a purification tag.

2. The polypeptide of claim 1, which, in presence of calcium ions, exhibits hydrolysis activity against a substrate of phosphoric acid swollen Avicel at least under conditions of 70° C. and pH 6.

3. A glycoside hydrolase mixture, comprising the polypeptide of claim 1 and at least one other glycoside hydrolase.

4. The glycoside hydrolase mixture of claim 3, further comprising a glycoside hydrolase family 6 (GH6) cellobiohydrolase.

5. A method for producing a cellulose degradation product, the method comprising contacting a material comprising cellulose with the polypeptide of claim 1, to thereby produce a cellulose degradation product.

6. A method for producing a cellulose degradation product, the method comprising contacting a material comprising cellulose with the polypeptide of claim 2, to thereby produce a cellulose degradation product.

7. A method for producing a cellulose degradation product, the method comprising contacting a material comprising cellulose with the glycoside hydrolase mixture of claim 3, to thereby produce a cellulose degradation product.

8. The method of claim 5, wherein the material comprising cellulose is contacted with the polypeptide, and with a GH6 cellobiohydrolase.

9. The method of claim 6, wherein the material comprising cellulose is contacted with the polypeptide, and with a GH6 cellobiohydrolase.

10. The method of claim 7, wherein the material comprising cellulose is contacted with the glycoside hydrolase mixture, and with a GH6 cellobiohydrolase.

* * * * *